United States Patent
Kang et al.

(10) Patent No.: US 8,703,813 B2
(45) Date of Patent: Apr. 22, 2014

(54) COMPOUND WITH SPIRO CHIRAL CARBON BACKBONE, PREPARATION METHOD THEREOF, AND PHARMACEUTICAL COMPOSITION CONTAINING THE SAME

(75) Inventors: Heon-Joong Kang, Seongnam-si (KR); Jung-Rae Rho, Gunsan-si (KR); Jeong-Ho Hong, Seoul (KR); Seung-Bum Park, Seoul (KR); Chan-Soo Shin, Seoul (KR); Jae-Hwan Lee, Seoul (KR); Jun-Young Hong, Seoul (KR); Eun-O Kim, Seoul (KR); Jeong-Ah Kim, Daegu (KR); Sang-Mi Oh, Siheung-si (KR)

(73) Assignee: SNU R & DB Foundation (KR)

( * ) Notice: Subject to any disclaimer, the term of this patent is extended or adjusted under 35 U.S.C. 154(b) by 328 days.

(21) Appl. No.: 13/126,979

(22) PCT Filed: Oct. 30, 2009

(86) PCT No.: PCT/KR2009/006357
§ 371 (c)(1),
(2), (4) Date: Apr. 29, 2011

(87) PCT Pub. No.: WO2010/050783
PCT Pub. Date: May 6, 2010

(65) Prior Publication Data
US 2011/0218240 A1    Sep. 8, 2011

(30) Foreign Application Priority Data

Oct. 31, 2008  (KR) .......................... 10-2008-0107821
Oct. 30, 2009  (KR) .......................... 10-2009-0104124

(51) Int. Cl.
*C07D 307/94*  (2006.01)
*A61K 31/35*   (2006.01)

(52) U.S. Cl.
USPC .......................................... 514/459; 549/345

(58) Field of Classification Search
USPC ........................................................ 549/345
See application file for complete search history.

(56) References Cited

U.S. PATENT DOCUMENTS 5,328,929 A  *  7/1994  Pettit et al. .................... 514/463
7,485,631 B2 *  2/2009  Razler et al. .................. 514/183

FOREIGN PATENT DOCUMENTS

JP   07-138261    5/1995
JP   2007-070364  3/2007

OTHER PUBLICATIONS

International Search Report_PCT/KR2009/006357 dated Jul. 15, 2010.

* cited by examiner

*Primary Examiner* — Noble Jarrell
*Assistant Examiner* — Raymond Covington
(74) *Attorney, Agent, or Firm* — Cantor Colburn LLP

(57) ABSTRACT

Provided is a compound having a spiro chiral carbon backbone, a stereoisomer thereof, an enantiomer thereof, an in vivo hydrolysable precursor thereof, or a pharmaceutically acceptable salt thereof. The compound having the spiro chiral carbon backbone has excellent osteoblast differentiation activity, mast cell inhibitory activity, and fatty acid synthesis inhibitory activity in the liver. Therefore, the compound can be expected to play an innovative role in treatment of osteoporosis, fatty liver, and obesity.

12 Claims, 16 Drawing Sheets

COMPOUND WITH SPIRO CHIRAL CARBON BACKBONE, PREPARATION METHOD THEREOF, AND PHARMACEUTICAL COMPOSITION CONTAINING THE SAME

TECHNICAL FIELD

The present invention relates to a novel compound with a spiro chiral carbon backbone, a preparation method thereof, and a pharmaceutical composition containing the same.

BACKGROUND ART

Recent rapid economic growth and medical development led to hypernutrition and an increase in elderly population, resulting in obesity and a sudden increase in fatty liver patients due to the obesity and an increase in osteoporosis suffers due to aging.

For a long time, adipose tissue has been thought to protect bodily tissue and preserve body heat, and as a storage place of energy for physical activity. However, many recent study results are demonstrating that the adipose tissue performs an important role in physiology and genesis of the human body. In particular, facts have found that materials capable of regulating various physiological activities, such as, balancing energy, controlling blood sugar, regulating insulin sensitivity, generating blood vessels, and the like, for example, adipsin, TNFa, leptin, etc., are secreted in adipocytes, one after another, and thus, the adipocytes has been thought as a hub of regulating metabolism of the human body.

On the other hand, as serious social diseases were caused by obesity, development of medications for inhibiting formation of the adipocytes is actively proceeding. However, even though a rapid increase in non-alcoholic fatty liver patients due to obesity acts seriously threatens the health of modern people, medication for effectively treating this has not been developed so far.

Osteoporosis is the result of collapsing the osteogenic balance between bone forming ability of osteoblasts and bone absorbing ability of osteoclasts. It has been known that the generation of the osteoblasts and the osteoclasts is regulated in view of hormones, external nutrients, and genes, but many genes that are directly causative of bone disease have not been yet found.

Most medications currently used in treatment methods inhibit the bone absorbing ability of bone cells to balance formation of bone cells. However, such medications have serious side effects and insignificant clinical effects, and thus, new-concept medications need to be developed. Even though many researchers have tried to develop medications capable of promoting formation of bone cells, that is, activation of osteoblasts, new medications having beneficial effects still have not been developed.

DISCLOSURE

Technical Problem

An object of the present invention is to provide a novel compound having very superior osteoblast differentiation ability.

Another object of the present invention is to provide a novel compound having excellent adipocyte differentiation inhibitory ability.

Still another object of the present invention is to provide a novel compound having selective activity for and excellent antagonistic activity against a liver-X-receptor (LXR).

Still another object of the present invention is to provide a novel compound inhibiting biosynthesis and absorption of fat in the liver.

Still another object of the present invention is to provide a pharmaceutical composition for treating osteoprosis, fatty liver, or obesity, containing the novel compound as an active component.

Technical Solution

In one general aspect, there are provided a compound of Formula 1 below, a stereoisomer thereof, an enantiomer thereof, an in vivo-hydrolysable precursor thereof, or a pharmaceutically acceptable salt thereof.

[Formula 1]

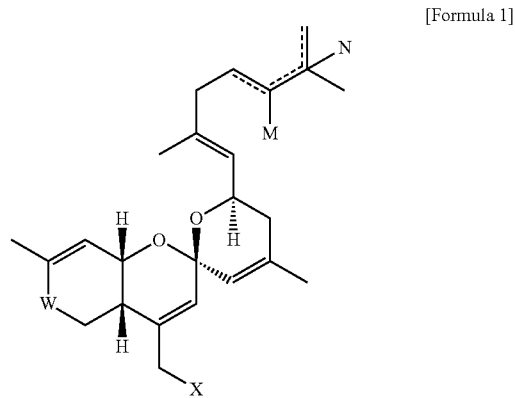

wherein:
W is CO or CHOR$_1$;
X is N$_3$, NHR$_2$, OR$_2$, SR$_2$, SeR$_2$ or TeR$_2$;
R$_1$ and R$_2$ are, independently, selected from hydrogen, straight or branched C1~C8 alkyl, C2~C8 alkenyl, C2~C8 alkynyl, C3~C8 cycloalkyl, C6~C20 aryl, C4~C20 heteroaryl, or

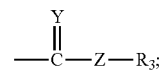

Y is O, S or NR$_4$;
Z is a single bond, NH, O, S, Se or Te;
R$_3$ and R$_4$ each are independently selected from hydrogen, straight or branched C1~C8 alkyl, C2~C8 alkenyl, C2~C8 alkynyl, C3~C8 cycloalkyl, C6~C20 aryl, or C4~C20 heteroaryl; and
M and N each are independently hydrogen, OH, or do not exist; wherein a carbon atom bonded to M or N forms a single bond or a double bond with other carbon atoms and the number of double bonds is one or less for each of the carbon atoms.

In another general aspect, there is provided a preparation method of the compound of Formula 1, the method including:
(a) cutting and drying the sponge *Phorbas* sp., followed by extraction using C1~C4 alcohol;
(b) partitioning the extract obtained from the step (a) by using water and methylene chloride, and then removing the solvent of the organic layer, followed by again partition using n-hexane and a mixture solution of methanol and water; and
(c) removing the solvent of the methanol aliquot layer obtained from the step (b), and then obtaining an aliquot by chromatography using silica as a stationary phase and using a methanol solution as an eluent, the methanol solution containing or not containing 20 weight % or less of water based on total weight thereof.

In still another general aspect, there is provided a pharmaceutical composition for treating osteoprosis including a compound of Formula 1, a stereoisomer thereof, an enantiomer thereof, an in vivo-hydrolysable precursor thereof, or a pharmaceutically acceptable salt thereof, as a pharmaceutically acceptable carrier and an active agent.

In still another general aspect, there is provided a pharmaceutical composition for treating fatty liver including a compound of Formula 1, a stereoisomer thereof, an enantiomer thereof, an in vivo-hydrolysable precursor thereof, or a pharmaceutically acceptable salt thereof, as a pharmaceutically acceptable carrier and an active agent.

In still another general aspect, there is provided a pharmaceutical composition for treating obesity including a compound of Formula 1, a stereoisomer thereof, an enantiomer thereof, an in vivo-hydrolysable precursor thereof, or a pharmaceutically acceptable salt thereof, as a pharmaceutically acceptable carrier and an active agent.

In still another general aspect, there is provided a pharmaceutical composition for antagonizing a liver-X-receptor (LXR) including a compound of Formula 1, a stereoisomer thereof, an enantiomer thereof, an in vivo-hydrolysable precursor thereof, or a pharmaceutically acceptable salt thereof, as a pharmaceutically acceptable carrier and an active agent.

Advantageous Effects

The compound of Formula 1 according to the present invention has very superior osteoblast differentiation ability, and thus it is expected that the compound of present invention can play a very innovative role in treatment of osteoprosis. In addition, the compound of Formula 1 according to the present invention has strong antagonistic efficacy against liver-X-receptors to inhibit synthesis of fat and absorption of fat in liver, and thus it is expected that the compound of the present invention can be very effective in treatment of fatty liver.

Furthermore, the compound of Formula 1 according to the present invention has excellent adipocyte differentiation inhibitory ability, and thus it is expected that the compound of the present invention can be used in treatment of obesity.

DESCRIPTION OF DRAWINGS

The above and other objects, features and advantages of the present invention will become apparent from the following description of preferred embodiments given in conjunction with the accompanying drawings, in which.

BEST MODE

Figure 1:
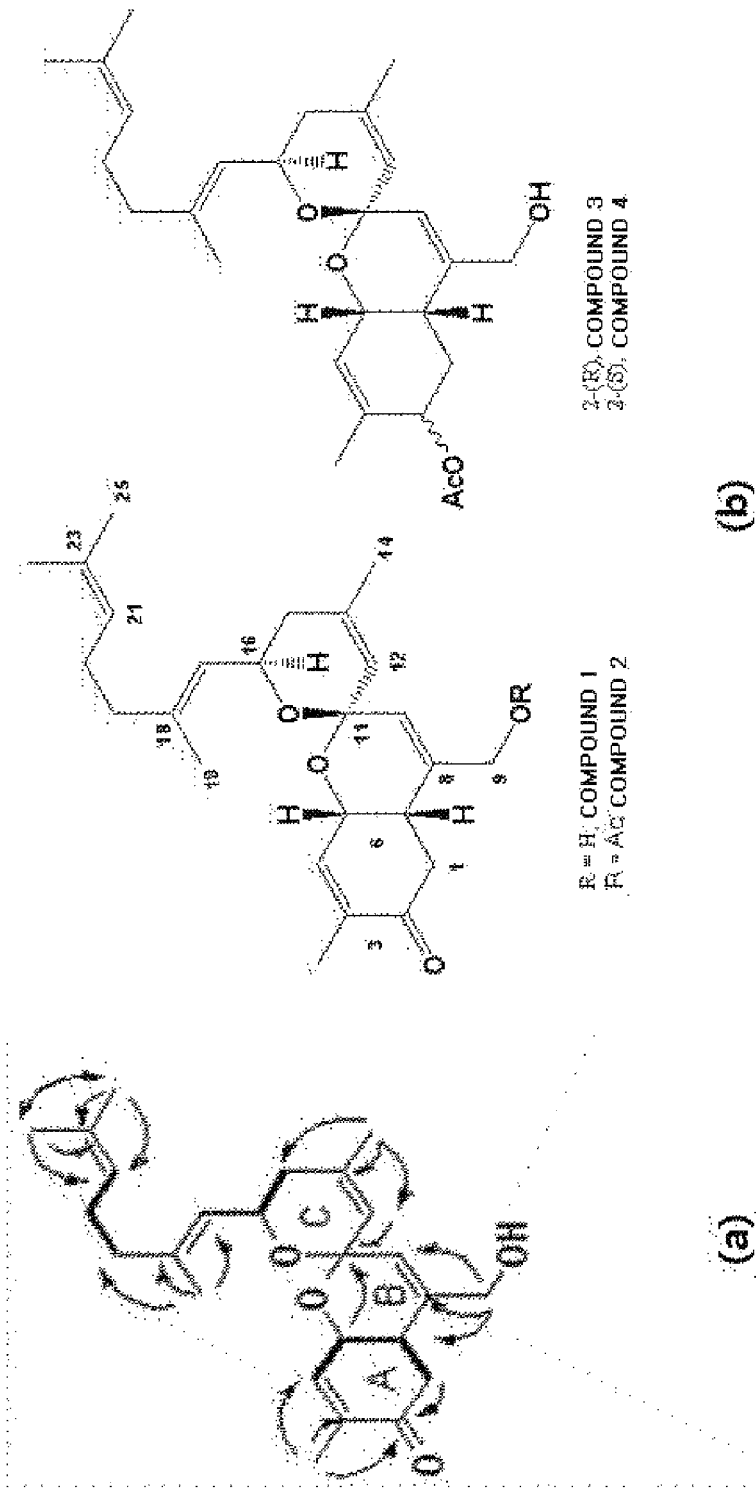
FIG. 1 shows hydrogen correlation (bold lines) and HMBC correlation (arrows displaying correlation binding from hydrogen nuclei to carbon nuclei) obtained by COSY experiment (a), and shows structures of the compounds 1 to 4 of the present invention (b)

The present invention is directed to a compound of Formula 1 below, a stereoisomer thereof, an enantiomer thereof, an in vivo-hydrolysable precursor thereof, or a pharmaceutically acceptable salt thereof.

[Formula 1]

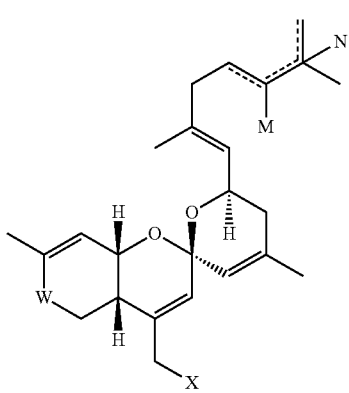

In Formula 1,

W is CO or CHOR$_1$;

X is N$_3$, NHR$_2$, OR$_2$, SR$_2$, SeR$_2$ or TeR$_2$;

R$_1$ and R$_2$ are, independently, selected from hydrogen, straight or branched C1~C8 alkyl, C2~C8 alkenyl, C2~C8 alkynyl, C3~C8 cycloalkyl, C6~C20 aryl, C4~C20 heteroaryl or

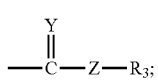

Y is O, S or NR$_4$;

Z is a single bond, NH, O, S, Se or Te;

R$_3$ and R$_4$ each are independently selected from hydrogen, straight or branched C1~C8 alkyl, C2~C8 alkenyl, C2~C8 alkynyl, C3~C8 cycloalkyl, C6~C20 aryl, or C4~C20 heteroaryl; and M and N each are independently hydrogen, OH, or do not exist; wherein a carbon atom bonded to M or N forms a single bond or a double bond with other carbon atoms and the number of double bonds is one or less for each of the carbon atoms.

The compound of Formula 1 is separated from an extract material (KNUE116) from sponge *Phorbas* sp. lived in the country, or synthesized by using the separated compound as a starting material, and a novel compound having a spiro chiral carbon backbone. The compound of Formula 1 promotes differentiation of osteoblast innovatively, inhibit adipocyte differentiation ability remarkably, and suppress synthesis of fat and absorption of fat in the liver. Therefore, it is expected that the compound of Formula 1 can play an innovative role in treatment of osteoporosis, treatment of fatty liver, and treatment of obesity.

The compounds of Formula 1 are specifically exemplified as follows.

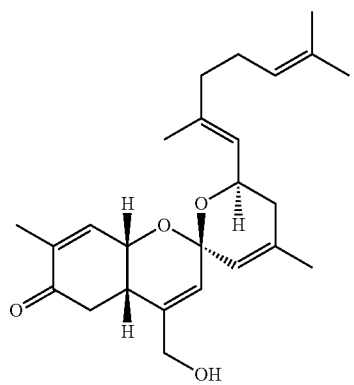

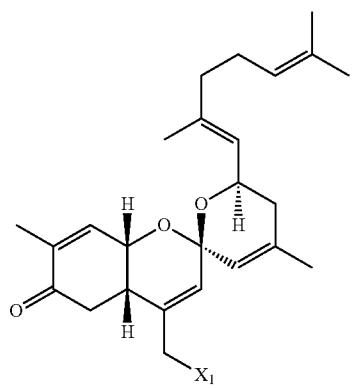

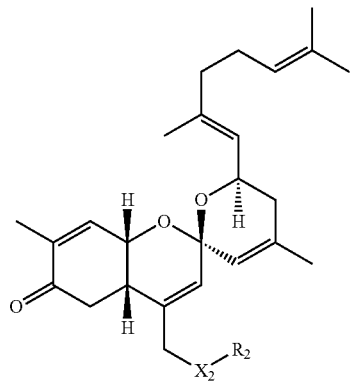

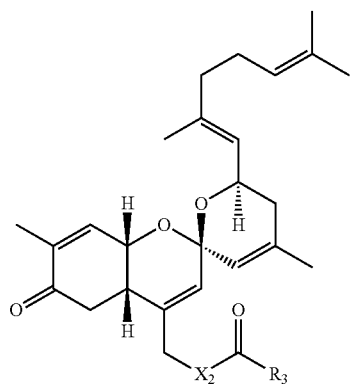

| 7 -continued | 8 -continued |
|---|---|
| 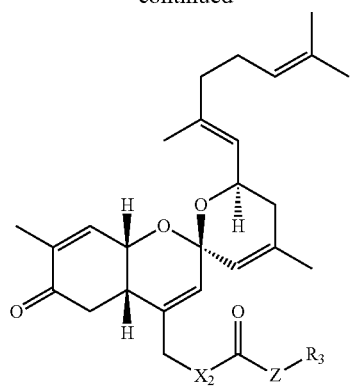 | 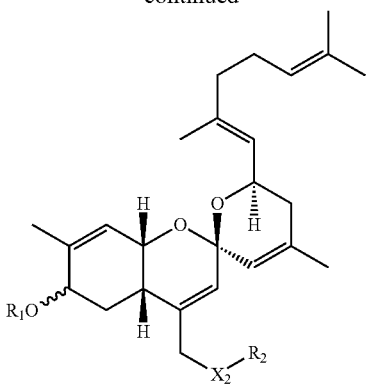 |
| 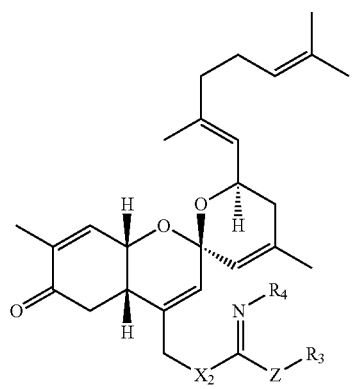 | 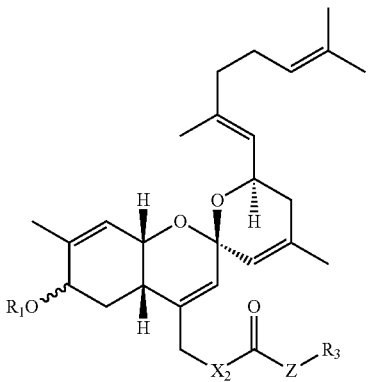 |
| 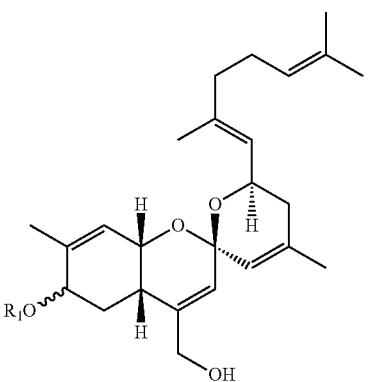 | 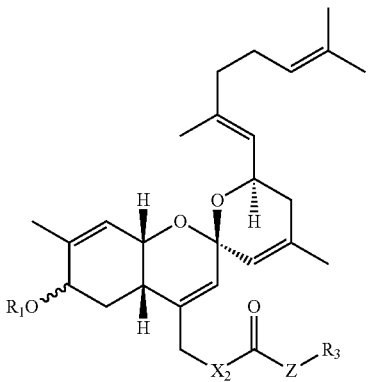 |
| 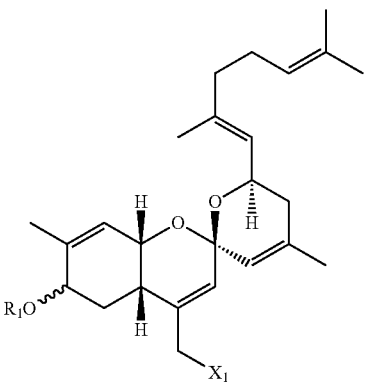 | 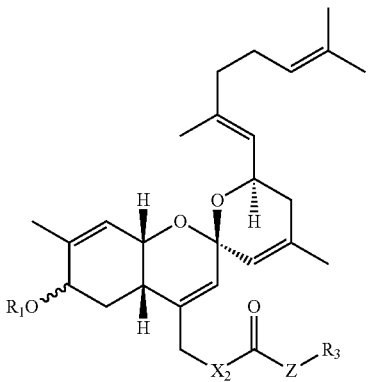 |

-continued

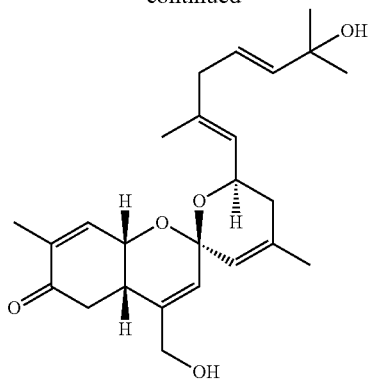

In the above formulas,
$X_1$ is $N_3$, $NH_2$, OH, SH, SeH, or TeH;
$X_2$ is NH, O, S, Se, or Te;
Z is a single bond, NH, O, S, Se, or Te;
$R_1$ is hydrogen, straight or branched C1~C8 alkyl, C2~C8 alkenyl, C2~C8 alkynyl, C3~C8 cycloalkyl, C6~C20 aryl, C4~C20 heteroaryl, or

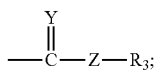

and
$R_2$, $R_3$ and $R_4$ each are hydrogen, straight or branched C1~C8 alkyl, C2~C8 alkenyl, C2~C8 alkynyl, C3~C8 cycloalkyl, C6~C20 aryl, or C4~C20 heteroaryl.

In a further preferred compound among the compounds of Formula 1 above, W is CO or $CHOR_1$; X is $N_3$, $NHR_2$, $OR_2$, $SR_2$, $SeR_2$ or $TeR_2$; $R_1$ and $R_2$ are independently selected from hydrogen, straight or branched C1~C8 alkyl, C2~C8 alkenyl, C2~C8 alkynyl, or

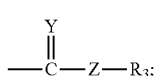

Y is O, S or $NR_4$; Z is a single bond, NH, O, or S; $R_3$ and $R_4$ each are independently selected from hydrogen, straight or branched C1~C8 alkyl, C2~C8 alkenyl, or C2~C8 alkynyl; and M and N each are independently hydrogen, OH, or do not exist, wherein a carbon atom bonded to M or N forms a single bond or a double bond with other carbon atoms and the number of double bonds is one or less for each of the carbon atoms.

In a further preferred compound among the compounds of Formula 1 above, wherein W is CO or $CHOR_1$; X is $N_3$, $OR_2$, or $SR_2$; $R_1$ and $R_2$ each are independently selected from hydrogen, straight or branched C1~C8 alkyl, C2~C8 alkenyl, C2~C8 alkynyl, or

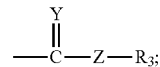

Y is O or S; Z is a single bond; $R_3$ is selected from hydrogen, straight or branched C1~C8 alkyl, C2~C8 alkenyl, or C2~C8 alkynyl; and M and N each are independently hydrogen, OH, or do not exist; wherein a carbon atom bonded to M or N forms a single bond or a double bond with other carbon atoms and the number of double bonds is one or less for each of the carbon atoms.

The compounds of Formula 1 are specifically exemplified as follows.

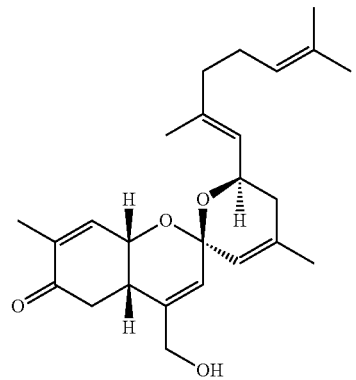

1

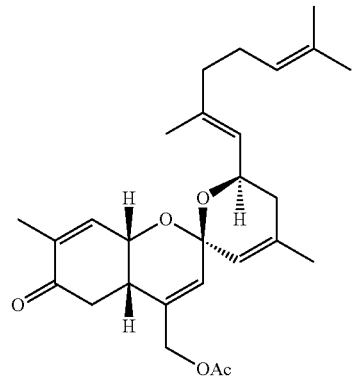

2

3
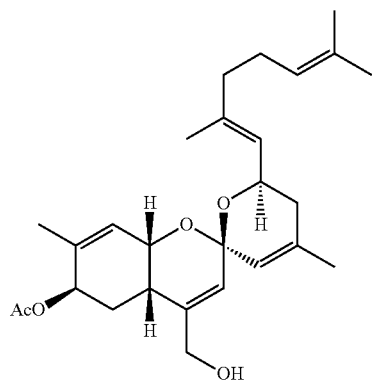
4
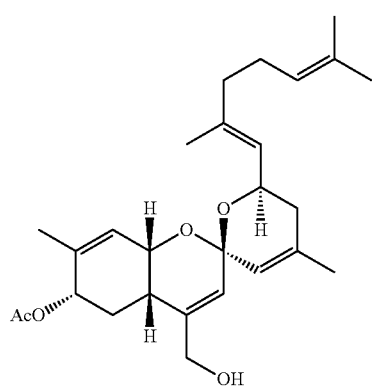
5
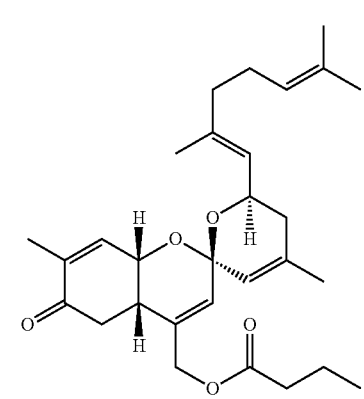
6
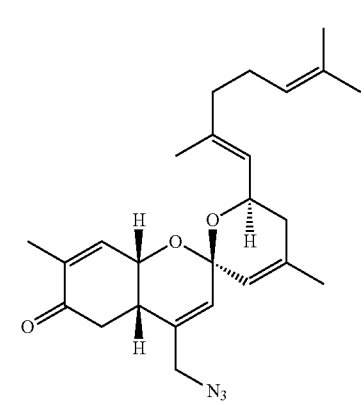
7
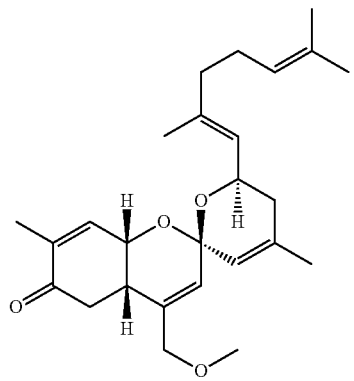
8
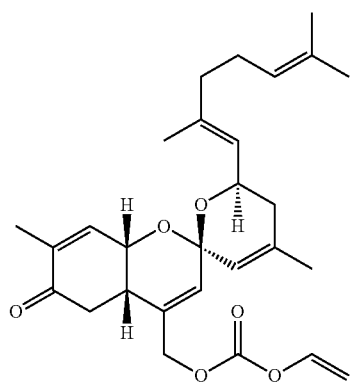
9
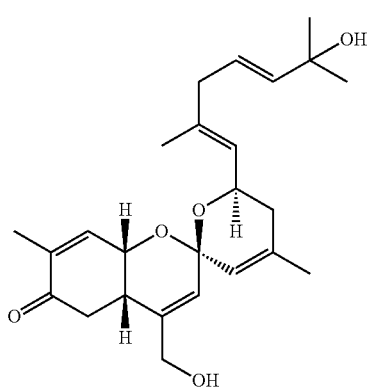
10
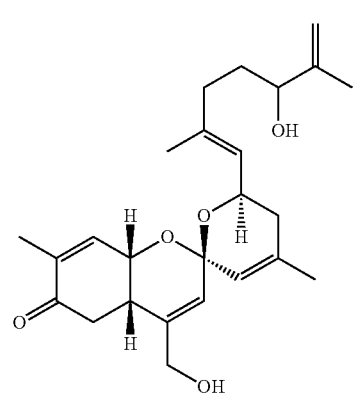
Further, the present invention provides a preparation method of the compound of Formula 1.

The prepared method of the present invention includes:

(a) cutting and drying the sponge *Phorbas* sp., followed by extraction using C1~C4 alcohol;

(b) partitioning the extract obtained from the step (a) by using water and methylene chloride, and then removing the solvent of the organic layer, followed by again partition using n-hexane and a mixture solution of methanol and water; and (c) removing the solvent of the methanol aliquot layer obtained from the step (b), and then obtaining an aliquot by chromatography using silica as a stationary phase and using a methanol solution as an eluent, the methanol solution containing or not containing 20 weight % or less of water based on total weight thereof.

Also, the preparing method may further includes (d) purifying the aliquot obtained from the step (c), after the step (c).

In the step (a), freeze-drying may be used for the drying, and methanol may be used for the C1~C4 alcohol. The extraction may be performed at room temperature, and preferably for 2 hours or more.

In the step (b), the mixture solution of methanol and water may contain 60~90 weight % of methanol and 10~40 weight % of water based on total weight of the solution.

In the step (c), reverse phase flash chromatography may be performed. The chromatography may be performed once or more in the order of from the eluent having the highest polarity to the eluent having the lowest polarity, by using a mixture solution of water and methanol having a higher polarity as the eluent, before using the methanol solution containing or not containing 20 weight % or less of water based on total weight of the eluent as the eluent. In particular, a mixture liquid of water and methanol may be used for the eluent.

In the step (d), the purifying may be performed by a high performance liquid chromatography (HPLC), and as the eluent, a mixture liquid of 50~80 weight % of acetonitrile (ACN) and 20~50 weight % of water based on total weight of the eluent may be used.

Meanwhile, the compounds of Formula 1 of the present invention may be synthesized by using the compounds separated through the above methods as a starting material and by the method, such as esterification reaction, azide substitution reaction, etherification reaction, or the like.

In addition, the present invention is directed a pharmaceutical composition for treating osteoprosis, fatty liver, and obesity, including a compound of Formula 1, a stereoisomer thereof, an enantiomer thereof, an in vivo-hydrolysable precursor thereof, or a pharmaceutically acceptable salt thereof, as a pharmaceutically acceptable carrier and an active agent.

In addition, the present invention provides a pharmaceutical composition for antagonizing a liver-X-receptor (LXR) including a compound of Formula 1, a stereoisomer thereof, an enantiomer thereof, an in vivo-hydrolysable precursor thereof, or a pharmaceutically acceptable salt thereof, as a pharmaceutically acceptable carrier and an active agent.

In the pharmaceutical composition, the pharmaceutically acceptable salt may be vehicle or medium usable in administration of medications, and any material that generally used in the art may be used without limitation. For example, solvent, dispersant, fillers, extenders, binders, wetting agents, disintegrants, surfactants, or the like may be used.

The pharmaceutical composition of the present invention may be formulated in a format of oral formulation such as powder, granule, tablet, capsule, suspension, emulsion, syrup, aerosol, or the like, external application, suppository, sterile injectable solution, or the like.

The dosage of the compound of Formula 1, the stereoisomer thereof, the enantiomer thereof, the in vivo-hydrolysable precursor thereof, or the pharmaceutically acceptable salt thereof, of the present invention may vary depending on conditions, body weights, and degrees of diseases of patients, formulation types of medications, routes of administration, and periods of administration, but may be properly selected by those skilled in the art. For example, 0.01 mg/kg to 200 mg/kg of dosage may be administered per one day. The administration may be performed once a day, or several times a day. Accordingly, the dosage does not limit the scope of the present invention at any aspect.

The pharmaceutical composition of the present invention may be administered to mammals such as rats, mice, livestock, human, and the like through various routes. All types of administration known before may be used, for example, rectal, intravenous, intramuscular, subcutaneous, intrauterinedural, or intracerebroventricular injection may be used for administration.

BEST MODE

Hereinafter, embodiments of the present invention will be described in detail with reference to the accompanying drawings. However, the embodiments are used to exemplify the present invention, and the present invention may be variously modified and changed without being limited by the embodiments.

Example 1

Separation and Purification of Novel Compounds

Sponge *Phorbas* sp. lived in the country was collected by using skin scubas, cut to a size of about 10 cm or less, and freeze-dried for 3 days, to prepare dried materials having a dried weight of about 1 kg. 3.0 L methanol was added to the dried materials, and then extracting was performed at room temperature total twice for 2 days. The extract was partitioned using water and a methylene chloride solvent, and then the solvent was removed from the organic layer by vacuum evaporation, followed by partitioning using n-hexane and a mixture solution of 85 weight % of methanol and 15 weight % of water. The solvent was removed from the 85 weight % methanol aliquot layer, and an aliquot of about 5 g was obtained. Reverse-phase silica flash chromatography was performed on the obtained aliquot. Here, reverse-phase silica C18 was used as a stationary phase, and the eluent was used in the order of from high polarity to low polarity, that is, in the order of 50% water/50% methanol, 40% water/60% methanol, 30% water/70% methanol, 20% water/80% methanol, 10% water/90% methanol, 100% methanol, and 100% acetone. The osteoblast differentiation ability of the material corresponding to each layer was measured. The results demonstrated that the osteoblast differentiation ability was found in 10% water/90% methanol aliquot (116V), and 100% methanol aliquot (116VI), each of the two aliquots was obtained in an amount of about 1 g.

In order to purify compounds from the two aliquots having activities, reverse phase semi-prep HPLC was performed. First, chromatography was performed on the aliquot 116V under the following conditions, to obtain compounds 1, 9, and 10.

[column: YMC ODSC18, particle diameter: 5 μm, column size: 250×10 mm (length×diameter), elution rate: 2.0 ml/min, detector: a refractive index detector, eluent: a mixture liquid of 65 weight % acetonitrile (ACN) and 35 weight % water]

When 50 mg of this aliquot liquid was injected, components of orange-colored oil form were separated at retention times of about 33 minutes (compound 1), 15 minutes (compound 9), and 40 minutes (compound 10) in amounts of 25 mg, 1.5 mg, and 1.0 mg, respectively. The same HPLC was also used for the aliquot 116VI, but different developing solvent conditions were used to separate additive components. In this case, a mixture liquid of 70 weight % of acetonitrile and 30 weight % of water was used. The total developing time of each performance took about an hour and a half. When 5 mg of the aliquot liquid 116VI was injected once, a compound 2 having an orange-colored oil form, a compound 3, and finally a compound 4 were separated, purified and obtained at retention times of about 1 hour 10 minutes, about 1 hour 40 minutes, and finally 1 hour 57 minutes in amounts of 0.5 mg, 0.08 mg, and finally 0.004 mg.

Example 2

Analysis of Chemical Structures of Novel Compounds

First, hydrogen nuclear magnetic resonance spectra of the compounds 1 to 4, 9, and 10 obtained from the aliquot liquids 116V and 116VI were measured to check purities thereof, and then spectroscopic data were obtained by using the following instruments. A mass spectrometer (JMS700 spectrometer from Jeol Inc.) was used to measure molecular weights of respective compounds, and then a nuclear magnetic resonance spectrometer (VNMRS 500 spectrometer from Varian Inc.) was used to analyze precise chemical structures thereof. Besides, a Cary50 spectrometer (from Varian Inc.) and an FT_IR 4100 spectrometer (from JACSO Inc.) were used to measure ultraviolet adsorption bands and infrared adsorption bands of molecules of the compounds, respectively, and a P1010 polarizer (JASCO Inc.) was used to measure polarization angles thereof.

The compound 1 was separated as a pale orange-colored oil form, and high-performance FAB mass spectroscopic data ([M+H]$^+$ m/z 399.2533) identified that the compound 1 has a molecular formula of $C_{25}H_{34}O_4$. The compound 1 was supposed to contain a hydroxyl group and a carbonyl functional group from characteristic adsorption bands by infrared spectrum analysis at 3433 cm$^{-1}$ and 1680 cm$^{-1}$. C$^{13}$NMR and HNMR were used to determine a structure of the compound. Chemical shift values for the compound 1 were summarized in Table 1 below.

TABLE 1

| | Compound 1 (116-3) | |
|---|---|---|
| No | $\delta_C$ | $\delta_H$ (J in Hz) |
| 1 | 38.8, t | α 2.43, dd (16.1, 13.7) |
| | | β 2.57, dd (16.1, 3.9) |
| 2 | 200.7, s | |
| 3 | 139.5, s | |
| 4 | 15.9, q | 1.81, s |

TABLE 1-continued

| | Compound 1 (116-3) | |
|---|---|---|
| No | $\delta_C$ | $\delta_H$ (J in Hz) |
| 5 | 141.6, d | 6.68, br d (5.4) |
| 6 | 64.7, d | 4.49, dd (5.4, 3.4) |
| 7 | 34.7, d | 2.59, ddd (13.7, 3.9, 3.4) |
| 8 | 143.7, s | |
| 9 | 63.8, t | 4.03, d (14.7) |
| | | 4.07, d (14.7) |
| 10 | 124.7, d | 5.54, br s |
| 11 | 96.1, s | |
| 12 | 123.0, d | 5.28, br s |
| 13 | 138.7, s | |
| 14 | 22.8, q | 1.75, s |
| 15 | 36.4, d | α 1.85, dd (17.6, 3.4) |
| | | β 2.01, dd (17.6, 11.3) |
| 16 | 66.9, d | 4.74, ddd (11.3, 7.8, 3.4) |
| 17 | 125.8, d | 5.22, br d (7.8) |
| 18 | 142.0, s | |
| 19 | 16.9, q | 1.78, s |
| 20 | 40.6, t | 2.06, m |
| 21 | 27.5, t | 2.12, m |
| 22 | 125.0, d | 5.12, br t (7.4) |
| 23 | 132.6, s | |
| 24 | 17.8, q | 1.61, s |
| 25 | 25.9, q | 1.68, s |

ROESY experiment was performed to determine a relative stereo-structure of this compound. It was determined that rings A and B are bonded in a cis-configuration, from NOE between the hydrogen (4.49 ppm) and the hydrogen (2.59 ppm). The stereo-configuration of a ring C could be determined according to NOE information between the hydrogen (5.28 ppm) and the hydrogen (5.54 ppm) and between the hydrogen (5.28 ppm) and the hydrogen (2.43 ppm). Finally, the spatial configuration of the hydrogen on C-16 could be assumed from coupling constants (11.3, 7.8, 3.4 Hz) between nearby hydrogen atoms, which is indirectly demonstrated by the fact that H-19 methyl hydrogen has NOE relationships with H-5 and H-6.

Figure 2:
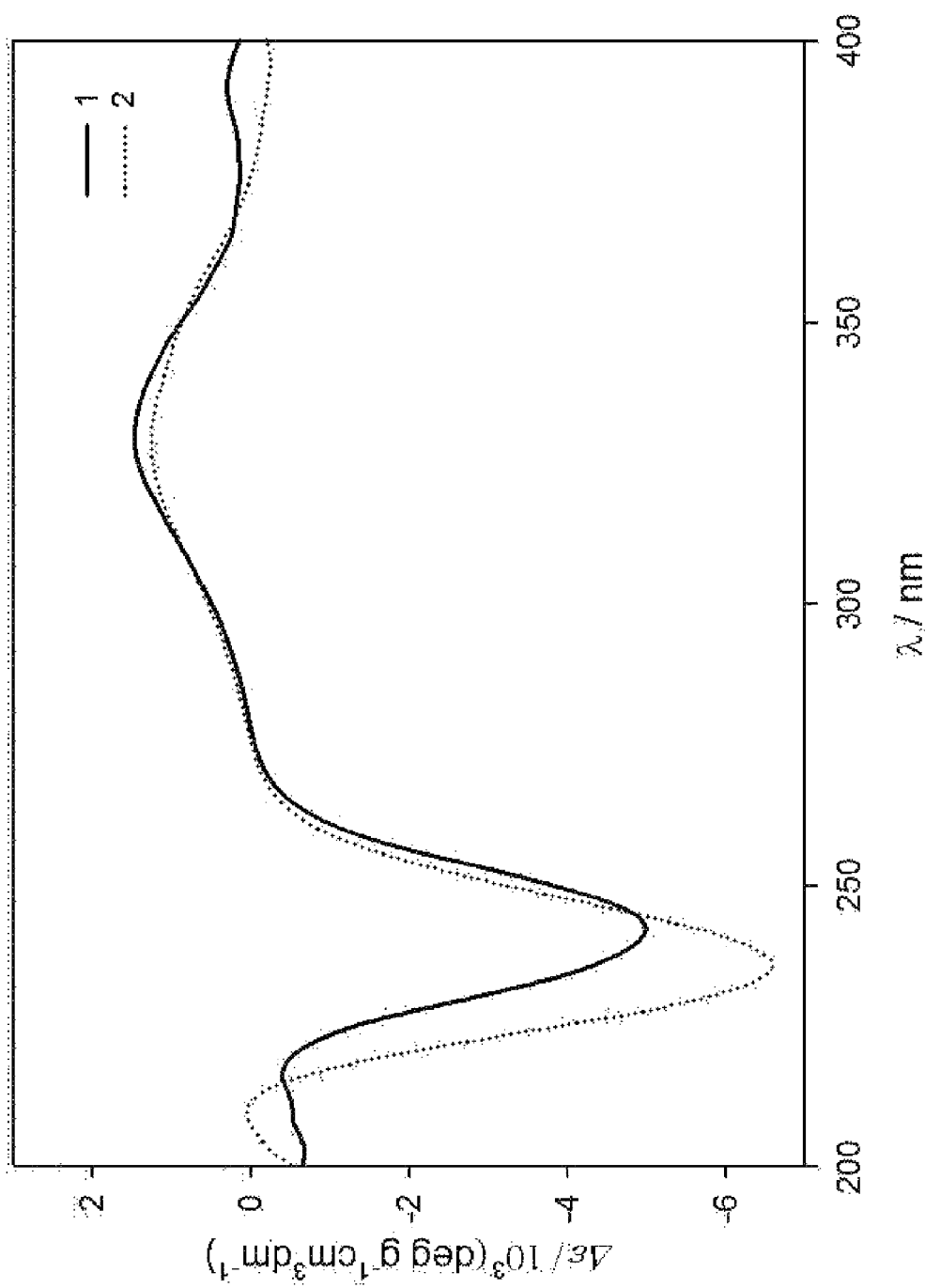
FIG. 2 shows circular dichroic spectra exhibited by the compounds 1 and 2 of the present invention.

The absolute stereo-chemical structure of the compound 1 was determined through circular dichroic spectrum (CD) analysis. The absolute stereo-configurations of chiral centers in cyclohexynone were determined according to Snatzke's sector rule. When a chiral center, C-7, in the cyclohexynone of ring A, has (S) absolute stereo-configuration, the compound 1 exhibits positive absorption at nπ* transition region (330 nm$^{-1}$~350 nm$^{-1}$) in the circular dichroic spectrum. Since the compound 1 exhibited positive adsorption at 330 nm$^{-1}$~350 nm$^{-1}$, the absolute configuration of C-7 in the compound 1 was determined as (S) stereo-configuration (FIG. 2).

Chemical structures of the other five compounds were determined by using the afore-mentioned method. Carbon NMR data and hydrogen NMR data of the respective three compounds were represented in Tables 2 to 4 below, and physical and spectroscopic data were tabulated in Table 5.

TABLE 2

| | Compound2 | Compound3 | Compound4 | Compound9 | Compound10 |
|---|---|---|---|---|---|
| 1 | 38.7, t | 29.5, t | 29.3, t | 38.8, t | 38.8, t |
| 2 | 200.3, s | 71.1, d | 73.2, d | 200.7, s | 200.7, s |
| 3 | 139.6, s | 138.5, s | 141.5, s | 139.5, s | 139.5, s |
| 4 | 15.9, q | 21.12, q | 19.0, q | 15.9, q | 15.9, q |
| 5 | 141.4, d | 127.2, d | 125.5, d | 141.6, d | 141.7, d |
| 6 | 64.5, d | 65.1, d | 65.0, d | 64.7, d | 64.7, d |
| 7 | 35.1, d | 30.1, d | 33.7, d | 34.7, d | 34.7, d |
| 8 | 138.8, s | 143.8, s | 143.9, s | 143.7, s | 143.7, s |

TABLE 2-continued

|  | Compound2 | Compound3 | Compound4 | Compound9 | Compound10 |
|---|---|---|---|---|---|
| 9 | 65.7, t | 63.9, t | 63.8, t | 63.8, t | 63.8, d |
| 10 | 127.9, d | 124.7, d | 124.8, d | 124.6, d | 124.7, d |
| 11 | 95.9, s | 95.5, s | 95.7, s | 96.1, s | 96.1, s |
| 12 | 122.6, d | 123.5, d | 123.5, d | 123.0, d | 123.0, d |
| 13 | 139.1, s | 138.4, s | 138.4, s | 138.7, s | 138.7, s |
| 14 | 22.9, q | 22.8, q | 22.9, q | 22.8, q | 22.8, q |
| 15 | 36.3, d | 36.4, d | 36.4, d | 36.3, d | 36.3, d |
| 16 | 66.9, d | 66.7, d | 66.7, d | 66.9, d | 66.9, d |
| 17 | 125.7, d | 125.8, d | 125.8, d | 126.3, d | 125.9, d |
| 18 | 142.0, s | 142.1, s | 142.1, s | 141.1, s | 142.0, s |
| 19 | 16.9, q | 16.9, q | 16.9, q | 16.9, q | 16.9, q |
| 20 | 40.6, t | 40.6, t | 40.6, t | 43.2, t | 36.6, t |
| 21 | 27.5, t | 27.5, t | 27.5, t | 125.1, d | 34.3, t |
| 22 | 125.0, d | 125.0, d | 125.0, d | 141.4, d | 76.2, d |
| 23 | 132.6, s | 132.6, s | 132.6, s | 71.1, s | 148.8, s |
| 24 | 17.8, q | 17.8, q | 17.8, q | 29.9, q | 111.5, d |
| 25 | 25.9, q | 25.9, q | 25.9, q | 29.9, q | 17.7, q |
| OAc(C=O) | 172.3, s | 172.7, s | 172.4, s |  |  |
| OAc (Me) | 20.7, q | 21.07, q | 20.9, q |  |  |

TABLE 3

|  | Compound 2 | Compound 3 | Compound4 |
|---|---|---|---|
| 1 | α 2.44, dd (14.2, 11.7) | α 1.73, ddd (14.2, 13.2, 3.9) | α 1.55, ddd (10.5, 11.5, 13.2) |
|  | β 2.60, dd (14.2, 3.4) | β 1.96, ddd (14.2, 3.4, 2.0) | β 2.12, m |
| 2 |  | 5.22, m | 5.37, dd (10.5, 5.9) |
| 4 | 1.81, s | 1.75, s | 1.72, s |
| 5 | 6.69, dd (5.4, 1.5) | 5.75, br d (5.4) | 5.65, br d (5.1) |
| 6 | 4.51, dd (5.4, 3.4) | 4.33, m | 4.27, m |
| 7 | 2.57, ddd (11.7, 3.4, 3.4) | 2.29, ddd (13.2, 3.4, 3.4) | 2.17, br d (13.2) |
| 9 | 4.54, dd (13.2, 1.5) | 4.02, dd (14.2, 1.0) | 4.03, dd (13.9, 1.2) |
|  | 4.65, dd (13.2, 1.5) | 4.06, dd (14.2, 1.0) | 4.08, dd (13.9, 1.2) |
| 10 | 5.60, br s | 5.51, d (1.0) | 5.51, d (1.2) |
| 12 | 5.28, br s | 5.23, m | 5.23, m |
| 14 | 1.75, s | 1.74, s | 1.75, s |
| 15 | α 1.85, dd (17.1, 3.4) | α 1.83, dd (17.1, 3.4) | α 1.83, dd (17.4, 3.2) |
|  | β 2.02, dd (17.1, 11.3) | β 2.00, dd (17.1, 11.3) | β 2.01, dd (17.4, 11.3) |
| 16 | 4.73, ddd (11.3, 8.3, 3.4) | 4.72, ddd (11.3, 8.3, 3.4) | 4.72, ddd (11.3, 8.3, 3.2) |
| 17 | 5.22, br d (8.3) | 5.21, br d (8.3) | 5.20, dd (8.3, 1.2) |
| 19 | 1.77, d (1.5) | 1.76, s | 1.75, d (1.2) |
| 20 | 2.05, m | 2.05, m | 2.05, m |
| 21 | 2.12, m | 2.12, m | 2.11, m |
| 22 | 5.12, br t (5.4) | 5.11, br t (7.1) | 5.11, br t (7.1) |
| 24 | 1.61, br s | 1.61, d (0.7) | 1.60, d (0.7) |
| 25 | 1.67, br s | 1.67, d (0.7) | 1.67, d (0.7) |
| OAc | 2.06, s | 2.06, s | 2.07, s |

TABLE 4

|  | Compound 9 | Compound 10 |
|---|---|---|
| 1 | α 2.43, dd (16.6, 13.9) | α 2.43, dd (16.6, 13.9) |
|  | β 2.58, dd (16.6, 3.6) | β 2.58, dd (16.6, 3.7) |
| 4 | 1.82, s | 1.81, d (1.5) |
| 5 | 6.71, ddd (4.1, 1.6, 1.6) | 6.71, dd (5.9, 1.5) |
| 6 | 4.50, m | 4.50, dd (5.9, 3.4) |
| 7 | 2.59, ddd (13.9, 3.6, 3.6) | 2.60, dd (13.9, 3.4) |
| 9 | 4.04, d (14.4) | 4.04, d (14.2) |
|  | 4.07, d (14.4) | 4.07, d (14.2) |
| 10 | 5.53, br s | 5.54, br s |
| 12 | 5.29, m | 5.29, m |
| 14 | 1.76, d (1.3) | 1.75, s |
| 15 | α 1.86, dd (17.4, 3.4) | α 1.86, dd (17.4, 3.4) |
|  | β 2.04, dd (17.4, 11.3) | β 2.03, dd (17.4, 11.3) |
| 16 | 4.75, ddd (11.3, 8.3, 3.4) | 4.75, ddd (11.3, 8.3, 3.4) |
| 17 | 5.27, br d (8.3) | 5.25, dd (8.3, 1.5) |
| 19 | 1.75, d (1.2) | 1.79, d (1.5) |
| 20 | 2.75, d (6.4) | 2.08, m |
| 21 | 5.59, dd (16.5, 6.4) | 1.65 td (7.8, 6.9) |
| 22 | 5.65, d (16.5) | 3.99, t (6.9) |
| 24 | 1.28, s | 4.82 brs; 4.92, br s |
| 25 | 1.28, s | 1.71, br s |

TABLE 5

|  | Compound 1 | Compound 2 | Compound 3 | Compound 4 | Compound 9 | Compound 10 |
|---|---|---|---|---|---|---|
| Moleculor Formula | $C_{25}H_{34}O_4$ | $C_{27}H_{36}O_5$ | $C_{27}H_{38}O_5$ | $C_{27}H_{38}O_5$ | $C_{25}H_{34}O_5$ | $C_{27}H_{38}O_5$ |
| Moleculor Weight | 398 | 440 | 442 | 442 | 414 | 414 |
| Color | Pale Orange | Pale Orange | Pale Yellow | Pale Yellow | Pale Yellow | Pale Yellow |
| Infrared | 3433, 2913, | 2920, 1743, | 3430, 2918, | 3387, 2914, | 3414, 2917, | 3413, 2925, |

TABLE 5-continued

| | Compound 1 | Compound 2 | Compound 3 | Compound 4 | Compound 9 | Compound 10 |
|---|---|---|---|---|---|---|
| Absorption Band ($cm^{-1}$) | 1680, 1000 | 1681, 1225 | 1735, 1238, | 1673, 1000 | 1678 | 1678 |
| Ultraviolet Absorption Band (nm) | 203, 230 | 203, 229 | 203 | 203 | 203, 227 | 204, 225 |
| Polarization Angle $[\alpha]_D^{25}$ in MeOH | −118.1 (c 0.15) | −63.9 (c 0.15) | −102.3 (c 0.10) | −148.7 (c 0.10) | −78.7 (c 0.15) | −57 (c 0.15) |
| Solubility | Easily Dissolved in Organic Solvent of Acetone, Methanol, DMSO, etc. | | | | | |

Example 3

Synthesis of Derivative of Compound 1 by Esterfication Reaction

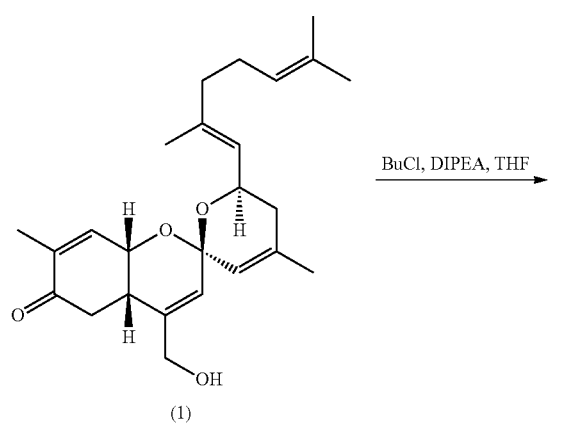

Example 4

Synthesis of Derivative of Compound 1 by Azide Substitution Reaction

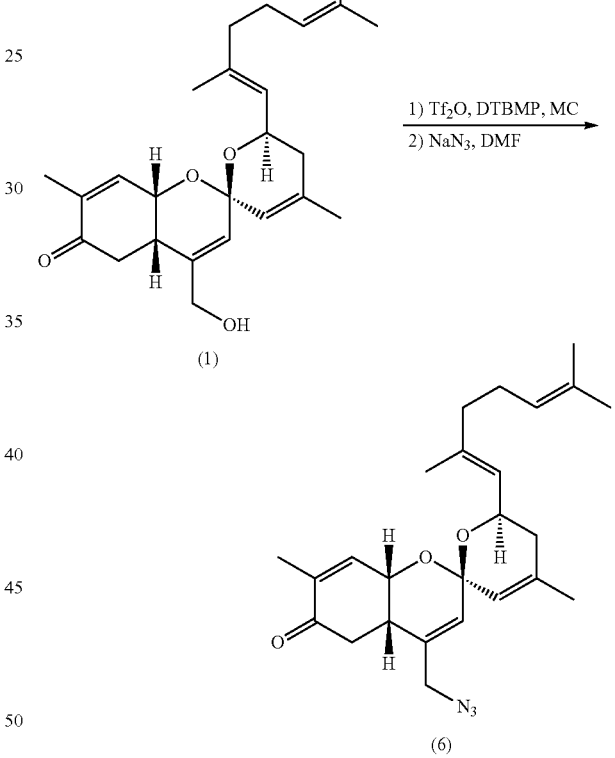

The compound 1 of the present invention was dissolved in tetrahydrofuran, and then the temperature was lowered to 0~5° C. Diisopropylethylamine and butyrylchloride were sequentially added thereto. The resultant material was stirred at 0~5° C. for 1 hour, and extracted by addition of ethylacetate and water, and then the organic solvent layer was separated and distilled. The residual material was purified by flash column chromatography to obtain the compound 5.

Compound 5 ($C_{29}H_{41}O_5$): $[M+H]^+ = 469.29$

The compound 1 of the present invention was dissolved in methylene chloride, and then the temperature was lowered to 0~5° C. diterbutylmethylprydine and trifluoromethanesulfonic anhydride were sequentially added thereto. The resultant material was stirred for 30 minutes, and extracted by the addition of methylenechloride and water. The organic solvent layer was separated and distilled, and the solvent was all evaporated. The residual material was again dissolved in dimethylformamide, and sodium azide was added thereto. The resultant material was stirred at room temperature for 3 hours, diluted by addition of methylenechloride, and then washed with water several times. The organic solvent layer was separated and distilled, and then the residual material was purified by flash column chromatography to obtain the compound 6.

Compound 6 ($C_{25}H_{34}N_3O_3$): $[M+H]^+ = 424.26$

Example 5

Synthesis of Ether Derivative of Compound 1

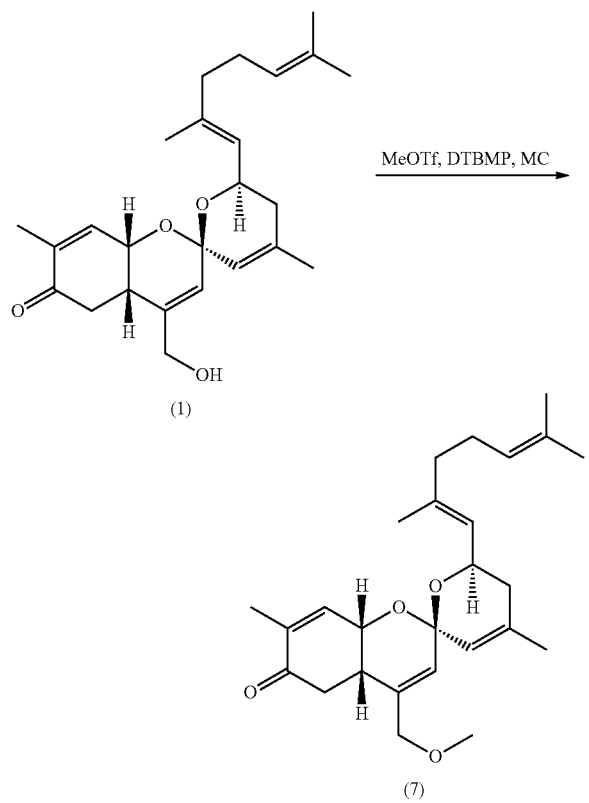

The compound 1 of the present invention and Diterbutyl-methylprydine were dissolved in methylene chloride, and then methanetrifluorosulfonate was added thereto. The resultant material was stirred at room temperature for 3 hours, and then the solvent was evaporated. The residual material was purified by flash column chromatography to obtain the compound 7.

Compound 7 ($C_{26}H_{37}O_4$): [M+H]$^+$=413.27

Example 6

Synthesis of Carbonate Derivative of Compound 1

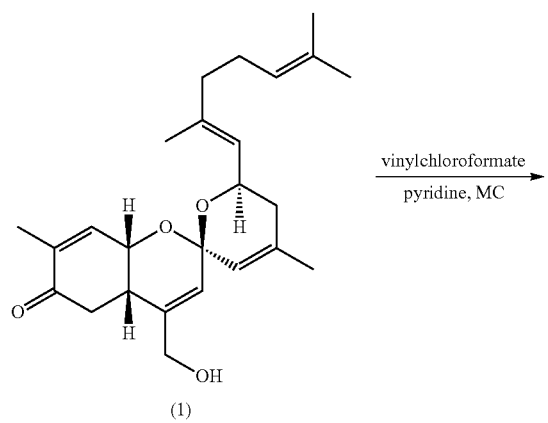

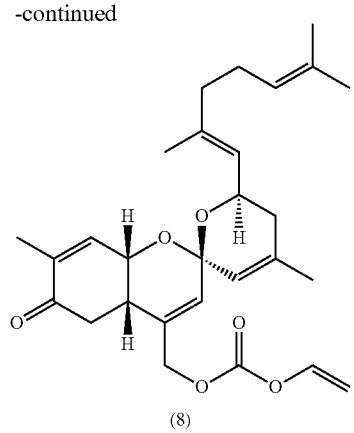

The compound 1 of the present invention was dissolved in methylene chloride, and then the temperature was lowered to 0~5° C. Pyridine and vinyl chloroformate were sequentially added thereto. The resultant material was stirred at room temperature for 1 hour, diluted with methylenechloride, and then washed with water. The organic solvent layer was separated and distilled, and then the resultant material was purified by flash column chromatography to obtain the compound 8.

Compound 8 (C28H37O6): [M+H]+=469.26

Experimental Example 1

Measurement on Osteoblast Formation Activity of Novel Compounds (Calcium Deposition Assay)

C3H/10T1/2 cells, which are mouse mesenchymal progenitor cells purchased from ATCC, were diluted in DMEM (Dulbecco's Modified Eagle Medium) medium containing 5.958 g/L HEPES, 3.7 g/L sodium bicarbonate, and 10% FBS (fetal bovine serum), and cultured in 24-well culture plates at a density of 4×10$^4$ cells/well, in the presence of 5% $CO_2$ at 37° C. for 2 days. The cultured cells were grown to 90~100% confluency in the culture plates, the cells were cultured in DMEM medium containing 10% FBS, to which 10 mM of β-glycerophosphate and 50µ/ml of ascorbic acid were added, in the presence of 5% CO2 at 37° C. for 6 days, to induce differentiation into osteoblast. The medium was exchanged every other day during differentiation. The C3H/10T1/2 cell line, in which differentiation into the osteoblast was induced, was washed with PBS (Phosphate Buffered Saline) once, and fixed with 70% ethanol at 20° C. for 1 hour. The cells after fixing were washed with cold PBS three times, and stained with 40 mM Alizarin Red S dye solution at room temperature for 20 minutes. The dye solution was removed and the cells were washed with distilled water three times in order to selectively observe only the cells differentiated into the osteoblast.

Figure 3:
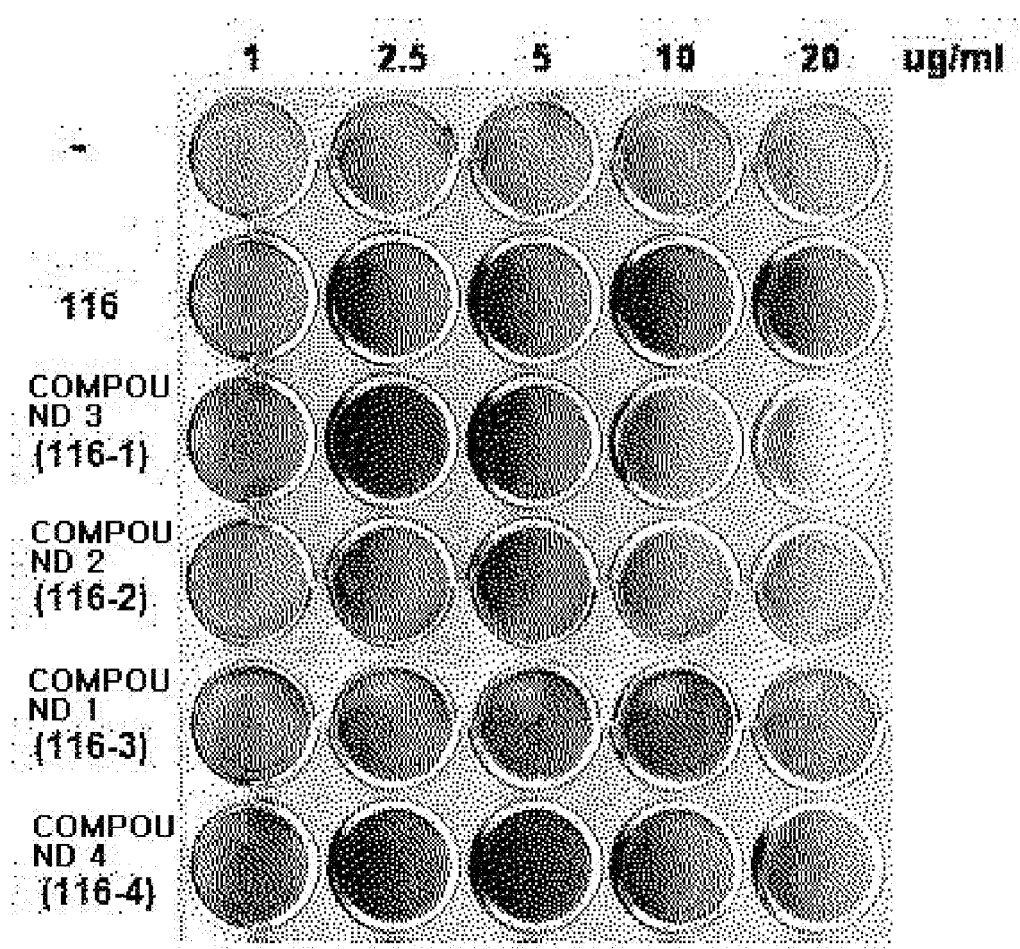
FIG. 3 shows a picture representing osteoblast differentiation ability measurement results of an extract aliquot 116V and the compounds 1 to 4 of the present invention (Experimental example 1)
Figure 4:
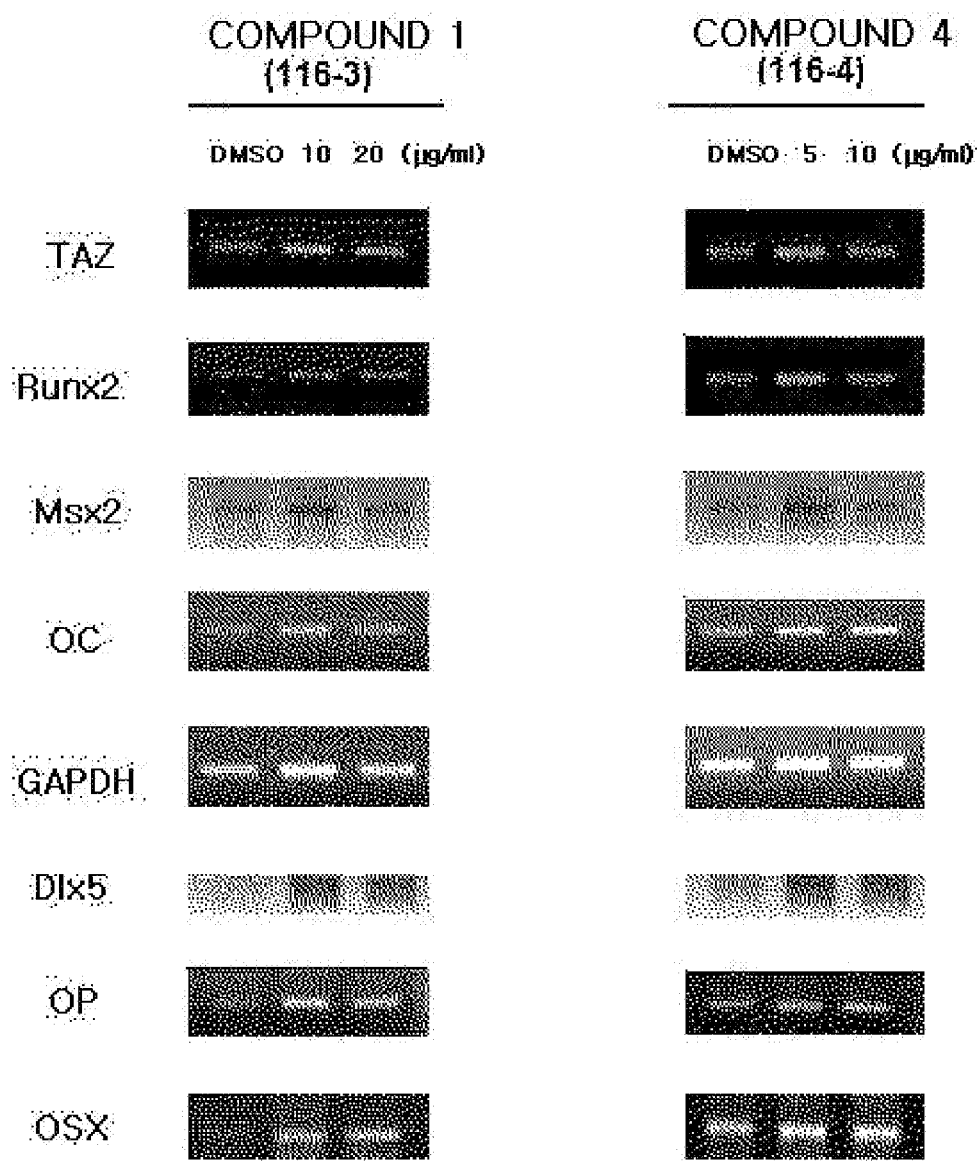
FIG. 4 shows RTPCR data that verify transcription degrees of osteoblast differentiation mark factors (Runx2, Osteocalcin, Msx2, etc.) through real time PCR(RTPCR), after treating C3H/10T1/2 cell lines with the compounds 1 to 4 of the present invention for 6 days (Experimental example 1)
Figure 5:
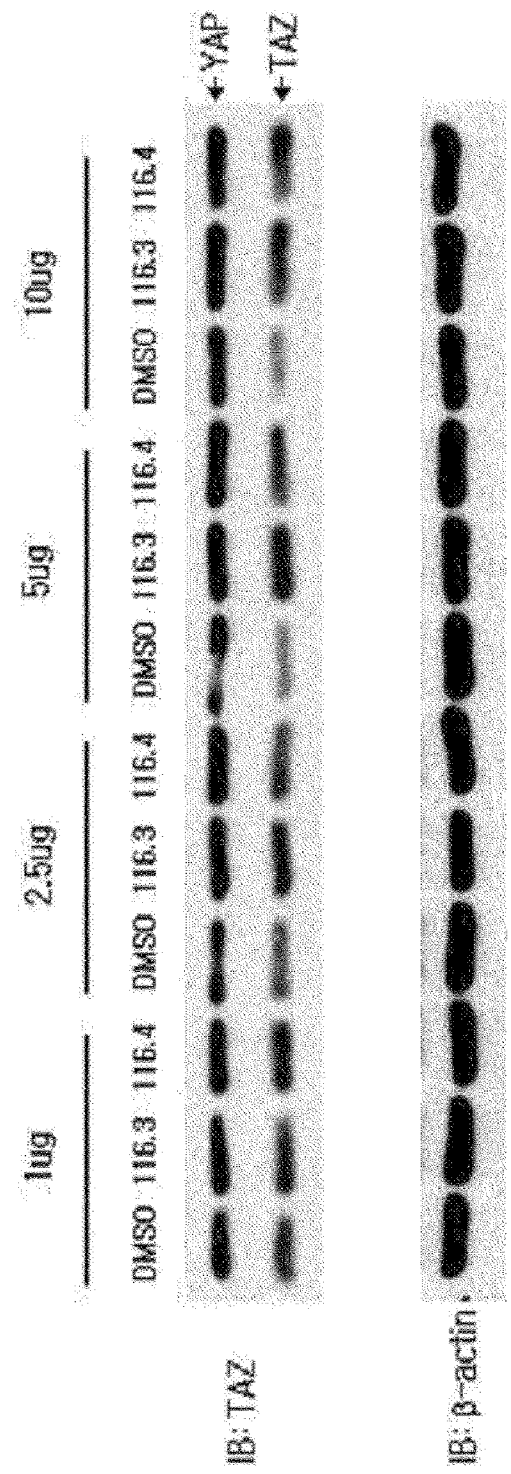
FIG. 5 shows Western blot data that verify protein expression of an osteoblast differentiation mark factor, TAZ, using Western Blot, after treating C3H/10T1/2 cell lines with the compounds 1 to 4 of the present invention for 6 days (Experimental example 1)
Figure 6:
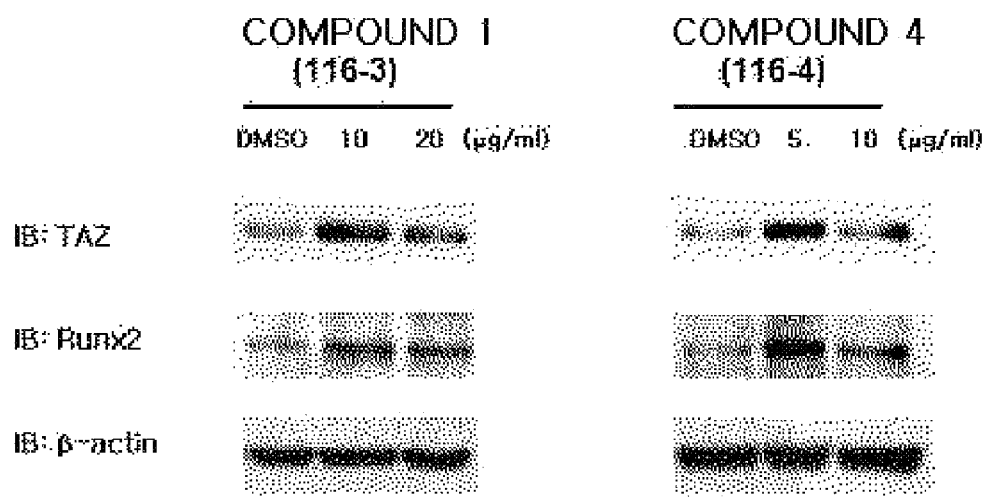
FIG. 6 shows Western blot data that verify protein expression of osteoblast differentiation mark factors, TAZ and Runx2 using Western Blot, after treating C3H/10T1/2 cell lines with the compounds 1 to 4 of the present invention for 6 days (Experimental example 1)
Figure 7:
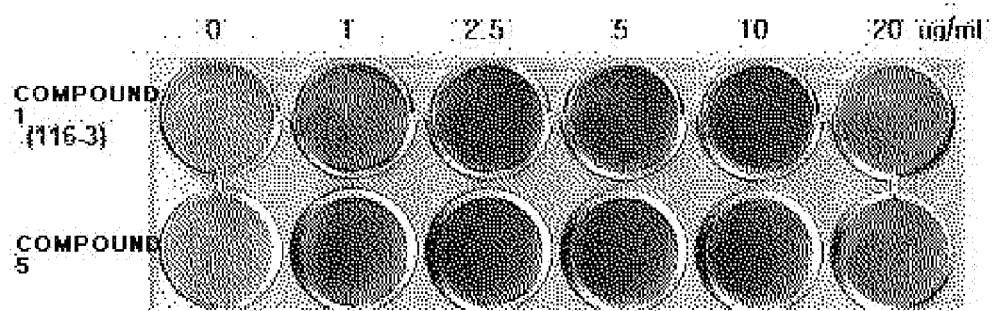
FIG. 7 shows a picture representing an osteoblast differentiation ability measurement result of the compound 5 of the present invention in Experimental example 1.

An aliquot 116V and an aliquot 116VI extracted and partitioned from sponges are dissolved in a DMSO solvent, and used to treat the C3H/10T1/2 cell line, mesenchymal progenitor cells, at concentrations of 1, 2.5, 5, 10, and 20 ug/ml. As a result, obsteoblast differentiation ability was shown to be remarkably increased in a concentration-dependent manner, and weak cytotoxicity was observed at a concentration of 20 ug/ml. Since then, the same experiment was performed on the compound (1163), the compound 2 (1162), the compound 3 (1161), and the compound 4 (1164), which were purely separated from the aliquots 116V and 116VI, and as a result, it could be confirmed that the osteoblast differentiation ability was increased in the compounds 1, 3, and 4. The concentrations at which the maximal activity was exhibited were a little different. The compound 3 (116-1) showed the maximum activity at 2.5 ug/ml, and cytotoxicity thereof was observable at the concentrations following that. The compound 1 (116-3) showed the activity remarkably increased at the concentrations of up to 10 ug/ml in a concentration-dependent manner and cytotoxicity at the concentration of 20 ug/ml, similarly to the activity of impurely separated aliquot 116V. The compound 4 showed the maximal activity at the concentration of 5 μg/ml, and cytotoxicity thereof was observed at the concentrations following that (FIG. 3). To study a mechanism with respect to osteoblast differentiation ability, the C3H/10T1/2 cell lines were treated with the compound 1 and the compound 4 for 6 days, respectively. It was found that the transcription degree of differentiation mark factors (Runx2, Osteocalcin, Msx2, etc.) of the osteoblast were remarkably increased, using real time PCR(RTPCR) (FIG. 4). Also, the C3H/10T1/2 cell lines were treated with the compound 1 and the compound 4 for 6 days, respectively. It was found that the protein expression of Runx2 and TAZ was increased, using Western Blot (FIGS. 5 and 6). Therefore, it could be found that the compounds of the present invention lead to an increase in the amounts of Runx2 and TAZ proteins through regulation after transcription and thus differentiation of the osteoblast could be promoted. Furthermore, it could be ascertained that combining of Runx2 and TAZ proteins was increased by treatment of the compounds and thus the activity of Runx2-mediated transcription was increased. The compound 5, which is an ester derivative of the compound 1 (1163), was synthesized in order to prepare a material having more excellent bioactivity, and the structure of the compound 5 obtained thus was determined. Further, through a calcium deposition assay on physiological activity (osteoblast differentiation ability) of the obtained derivative, it was found that the compound 5, which is a derivative of the compound 1, also promoted differentiation of the osteoblast in a similar degree as that of the compound 1 (FIG. 7). Therefore, the compounds of the present invention and derivatives thereof are expected to promote the differentiation of the osteoblast and thus play an innovative role in treatment of osteoporosis.

Experimental Example 2

Measurement on Adipocyte Differentiation Inhibitory Ability of Novel Compounds

C3H/10T1/2 cells, which are mouse mesenchymal progenitor cells purchased from ATCC, were diluted in DMEM (Dulbecco's Modified Eagle Medium) medium containing 5.958 g/L HEPES, 3.7 g/L sodium bicarbonate and 10% FBS (fetal bovine serum), and cultured in 24-well culture plates at a density of $4 \times 10^4$ cells/well, in the presence of 5% $CO_2$ at 37° C. for 2 days. When the cultured cells were grown to 90~100% confluency in the culture plates, the cells were cultured in DMEM medium containing 10% FBS, to which 5μ/ml insulin, 1 μM dexamethason, and 5 μM troglitazone were added, in the presence of 5% $CO_2$ at 37° C. for 8 days, to induce differentiation into adipocyte. The medium was exchanged every other day during differentiation. The C3H/10T1/2 cell line, in which differentiation into the adipocyte was induced, was fixed with 3.7% formaldehyde at room temperature for 30 minutes. An oil Red O solution dissolved in isopropanol at a concentration of 0.5% was diluted in distilled water at a ratio of 6:4, filtered through a 0.2 μm filter, and poured to the fixed cell line, which was stained for 1 hour. In order to observe only the cells differentiated into the adiopocyte, the dye solution was removed and the cells were washed with distilled water two times.

Figure 8:
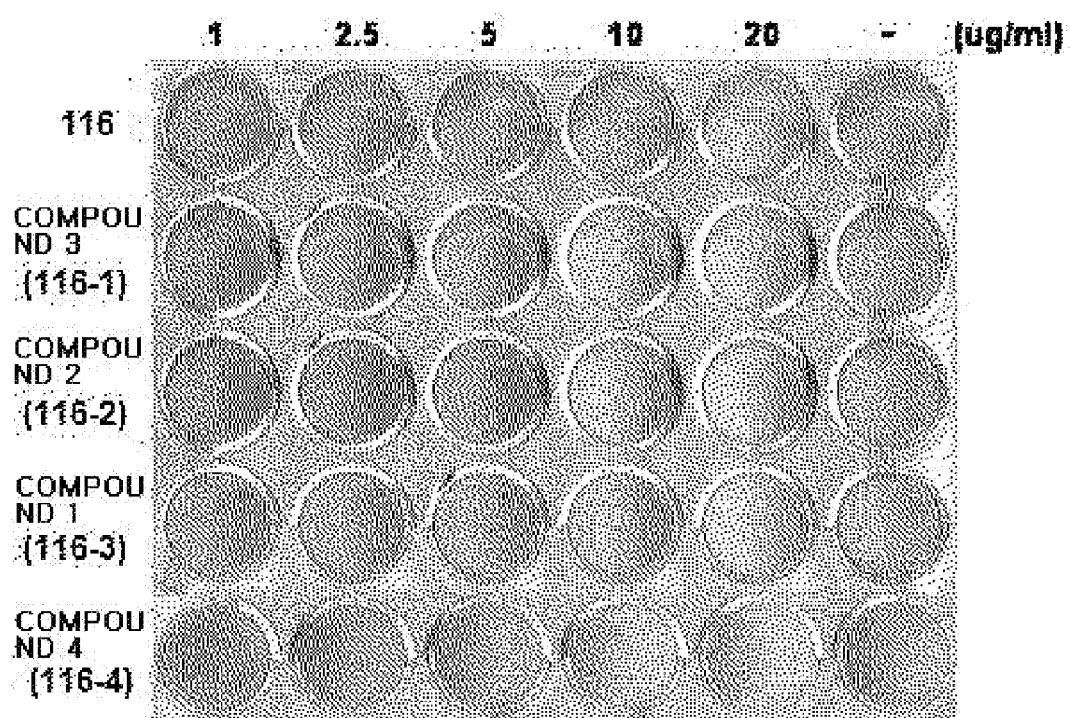
FIG. 8 shows a picture representing adipocyte (C3H/10T1/2) differentiation ability measurement results of the extract aliquot 116V and the compounds 1 to 4 of the present invention in Experimental example 2.
Figure 9:
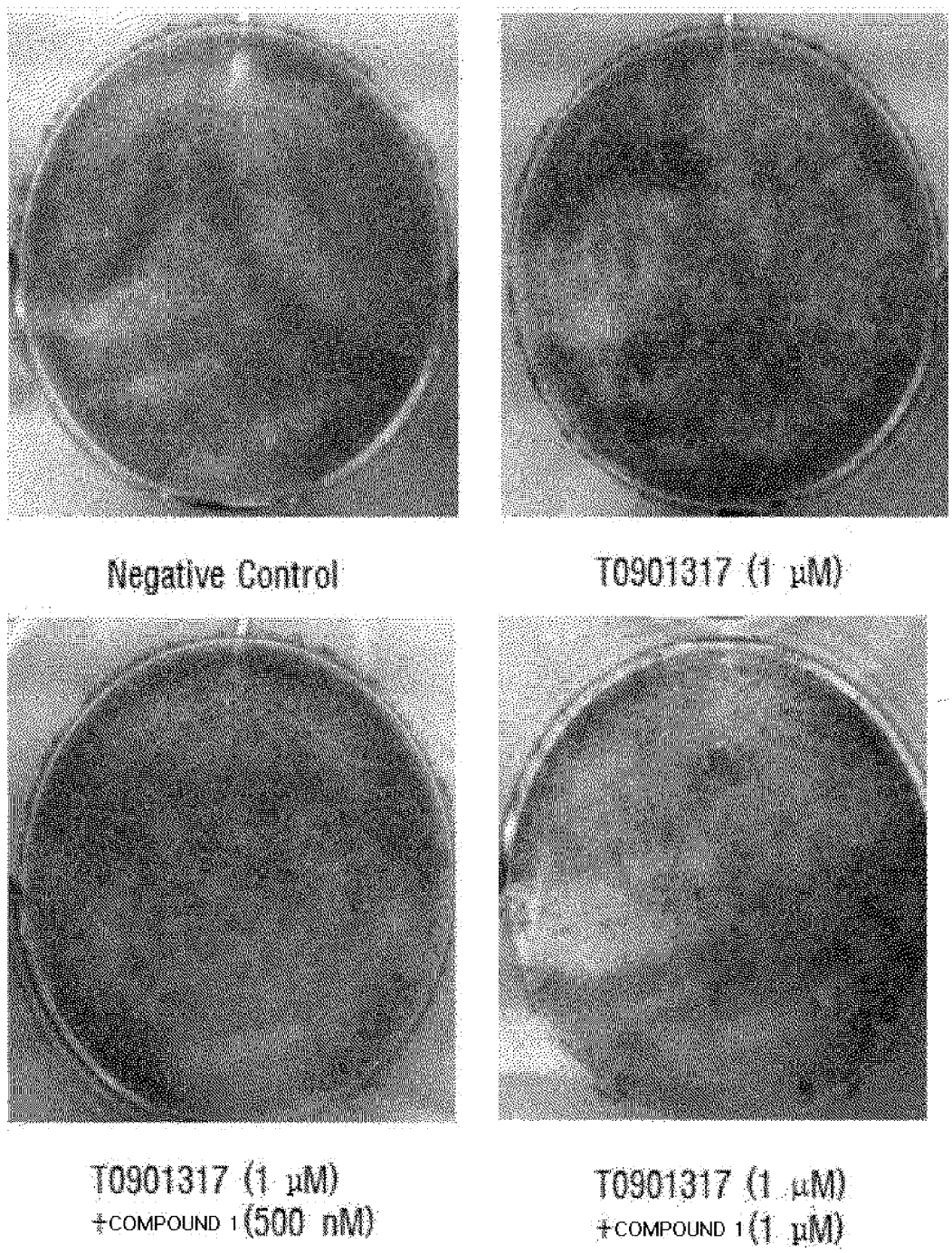
FIG. 9 shows a picture representing an adipocyte (3T3-L1) differentiation inhibitory ability measurement result of the compound 1 of the present invention in Experimental example 2.

116V specimen extracted from sponge was dissolved in DMSO solvent, and allowed to treat C3H/10T1/2 cell lines, which are mouse mesenchymal progenitor cells, at concentrations of 1, 2.5, 5, 10, and 20 μg/ml. The results showed that adipocyte differentiation ability was remarkably decreased in a concentration-dependent manner. Then, after specimens of the compound 1 (1163), the compound 2 (1162), the compound 3 (1161), and the compound 4 (1164), which were purely separated from the 116V and 116VI species were obtained, the same experiment was performed. The experimental results showed that adipocyte differentiation abilities of the compounds were remarkably decreased at the concentration of 10 μg/ml. In particular, the compound 1 (116-3) specimen exhibited the remarkable adipocyte differentiation inhibitory ability even at a low concentration (1 μg/ml), compared with the other species. Remarkable cytotoxicity was not observed in each of the specimens during differentiation of adipocytes (FIG. 8). As a result of testing efficacy of the compound 1 on 3T3-L1 cells, the compound 1 exhibited very superior adipocyte differentiation inhibitory ability even in these cells (FIG. 9).

Experimental Example 3

Measurement on Antagonistic Efficacy and Selectivity of Novel Compounds with Respect to Liver-X-Receptor (LXR)

Figure 10:
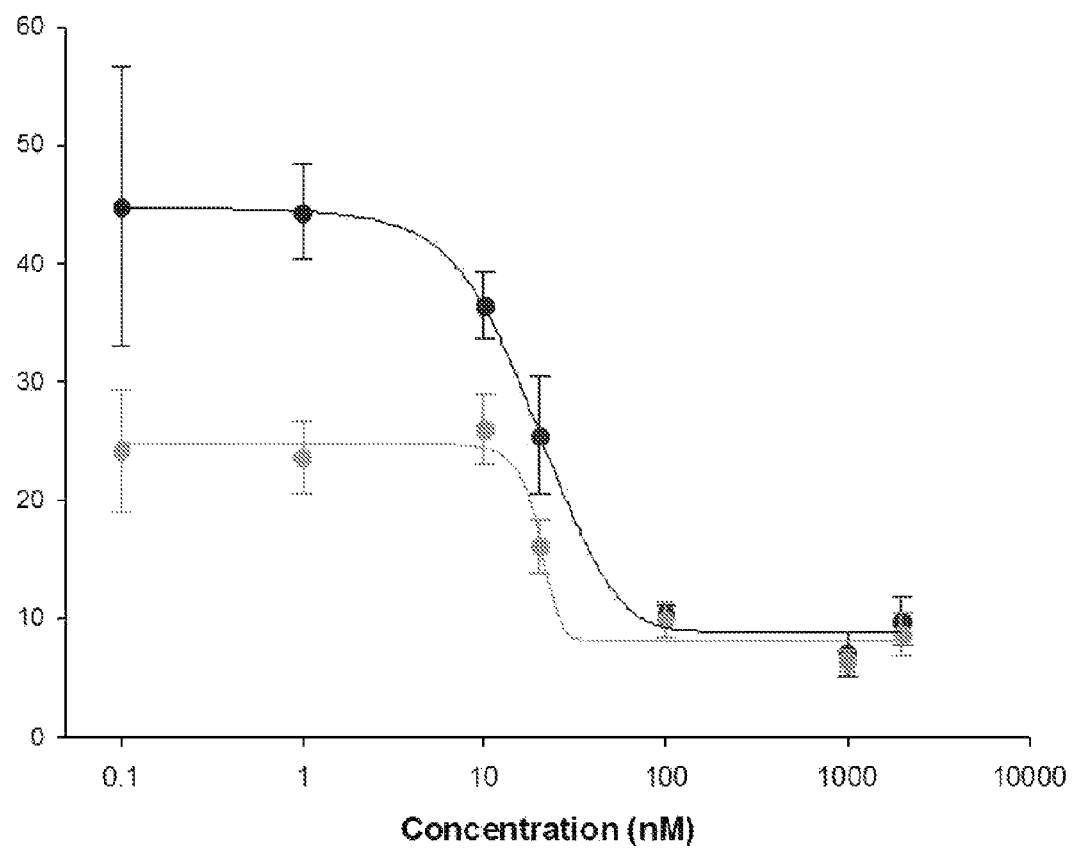
FIG. 10 shows a graph representing an antagonistic activity measurement result of the compound 1 of the present invention against an LXR nuclear receptor in Experimental example 3.
Figure 11:
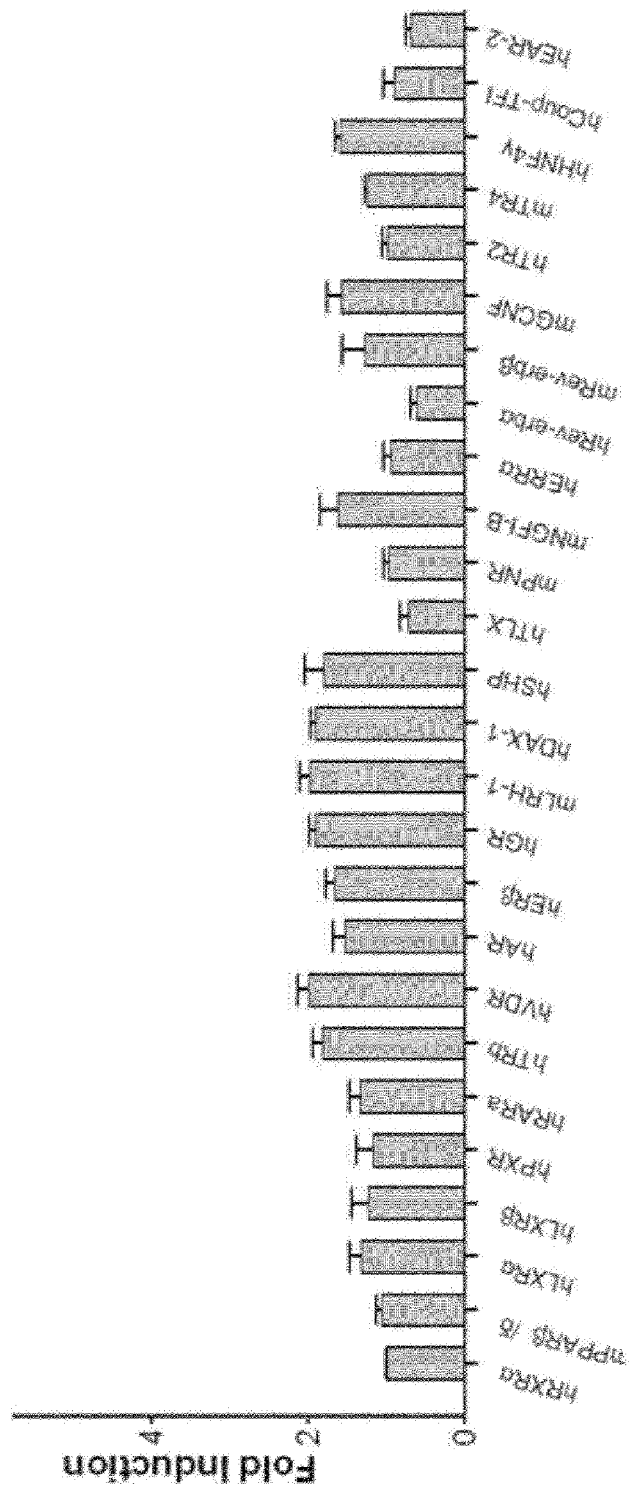
FIG. 11 shows a graph representing selective activity measurement results of the compound 1 of the present invention for various nuclear receptors in Experimental example 3.
Figure 12:
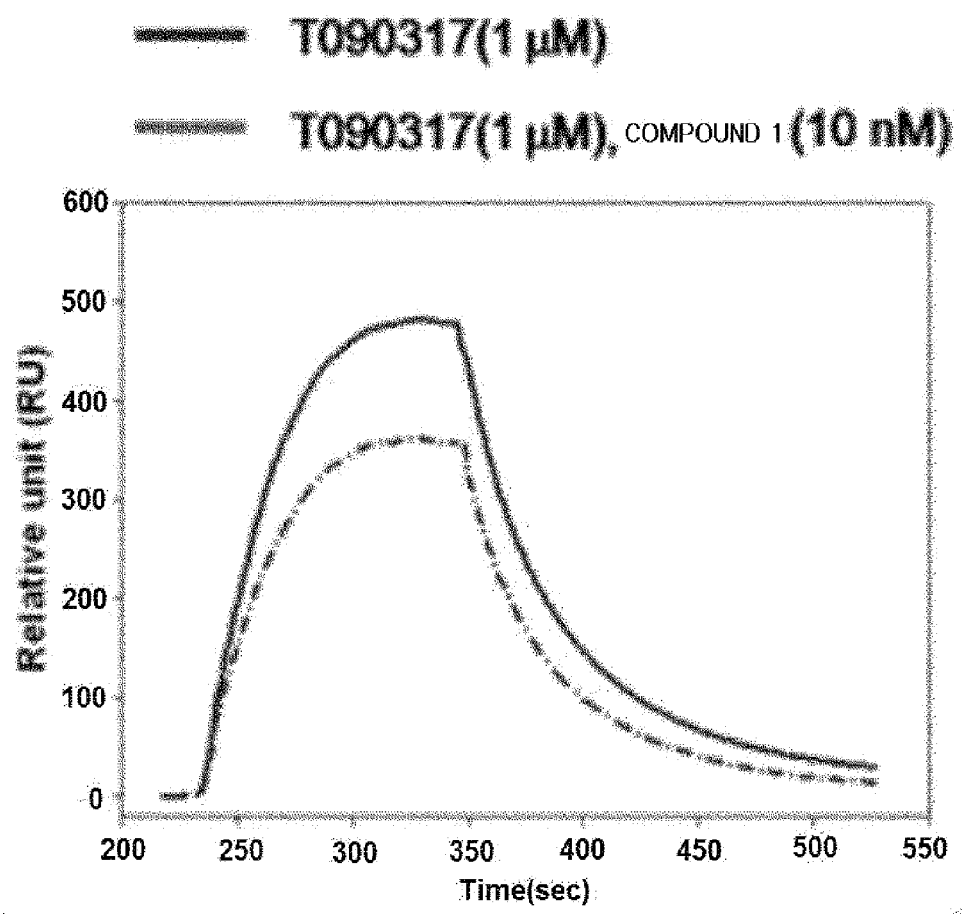
FIG. 12 shows a graph representing direct binding measurement results of the compound 1 of the present invention on the LXR nuclear receptor protein in Experimental example 3.

Animal cell line CV-1 was used in transfection search. Cells were cultured in DMEM medium within a cell culture device containing 5% carbon dioxide at 37° C. The medium contained 10% FBS (fetal bovine serum), 100 U/ml penicillin, and 100 μg/ml streptomycin. On day 1 of the experiment, CV 1 cells were seeded in 96 well plates at 5,000 cells/well. On day 2, the seeded cells were transfected with plasmid expressing GAL-hLXR, plasmid expressing Luciferase gene, and plasmid expressing β-galactocidase by using a transfection reagent, Superfect (QIAGEN). After 16 hours, the transfected cells were treated with the compound 1 dissolved in dimethylsulfoxide (DMSO) by the concentrations, together with the agonist, TO901317 (2.5 μM). Cells treated with dimethylsulfoxide having the final concentration of 1% were used as a negative control group, and cells treated with T0901317 having the final concentration of 500 nM were used as a positive control group. The cells were cultured for 24 hours, and lysed by using a lysis buffer. Luciferin was added to the cells to measure the luciferase activity using a luminometer. The β-galactosidase activity, after adding of an ONPG reagent, was measured using an ELISA reader. The measured Luciferase value was corrected by activity value of β-galactosidase. The results showed that the compound 1 had $IC_{50}$ values of 18.7 and 20.4 nM on LXRα and LXRβ, respectively (FIG. 10). In addition, the activities on various nuclear receptors were measured by using the same method, in order to measure selectivity for various nuclear receptors. However, the compound 1 never showed the activity on the other nuclear receptors (FIG. 11). Also, Biacore experiment proved that the compound 1 was directly bound with the LXR protein (FIG. 12).

Experimental Example 4

Measurement on Cytotoxicity of Novel Compounds

Figure 13:
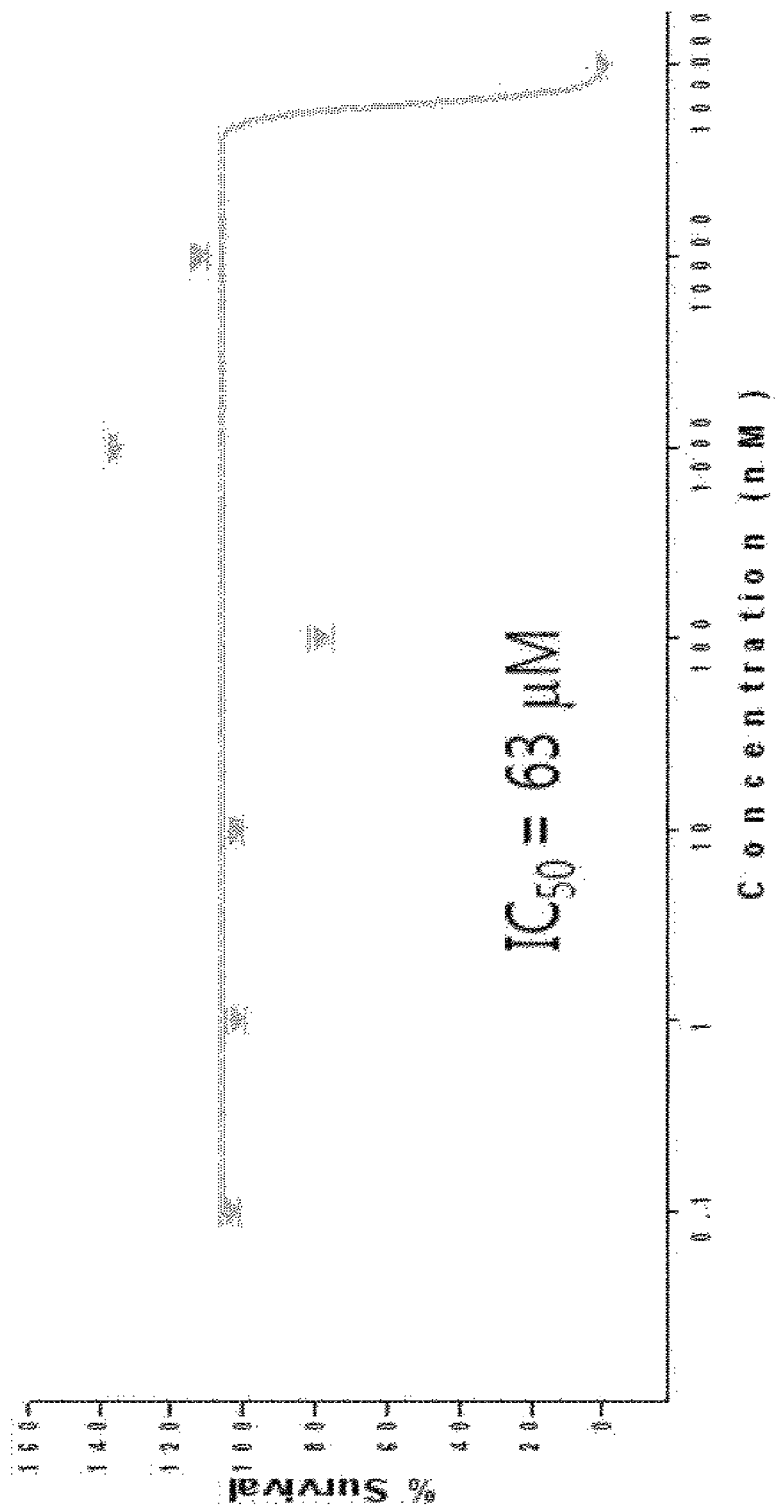
FIG. 13 shows a graph representing a cytotoxicity measurement result of the compound 1 of the present invention on mouse spleen cells in Experimental example 4.

Spleen cells of a mouse were used in measurement of cytotoxicity in abnormal cells. The spleen cells of the mouse were prepared as follows. The spleen from a 5~6-week age mouse was finely minced, and only floating spleen cells were filtered through a net having a pore size of 100 μm. Erythrocytes mixed with the spleen cells were lysed by using erythrocyte lysis buffer, and then removed by centrifugation, precipitation and washing of the cells. The prepared spleen cells were seeded in 96-well plates at a concentration of $5 \times 10^5$ cells/well. Here, the spleen cells were treated with the compound of Formula 1 for measurement of toxicity according to the concentrations. The next day, the cells cultured for 16-18 hours were treated with Cell Titer-Glo Luminescent Cell Viability Assay (Promega), and after 10 minutes, cell viability was measured using the luminometer. The compound 1 has been shown to have little cytotoxicity on normal cells by exhibiting a cytotoxicity $IC_{50}$ value of 63 μM on mouse spleen cells, which is 1000 times or more compared than an antagonistic concentration against LXR (FIG. 13).

Experimental Example 5

Verification on Function of Gene Expression by Novel Compounds in Liver Cells

Figure 14:
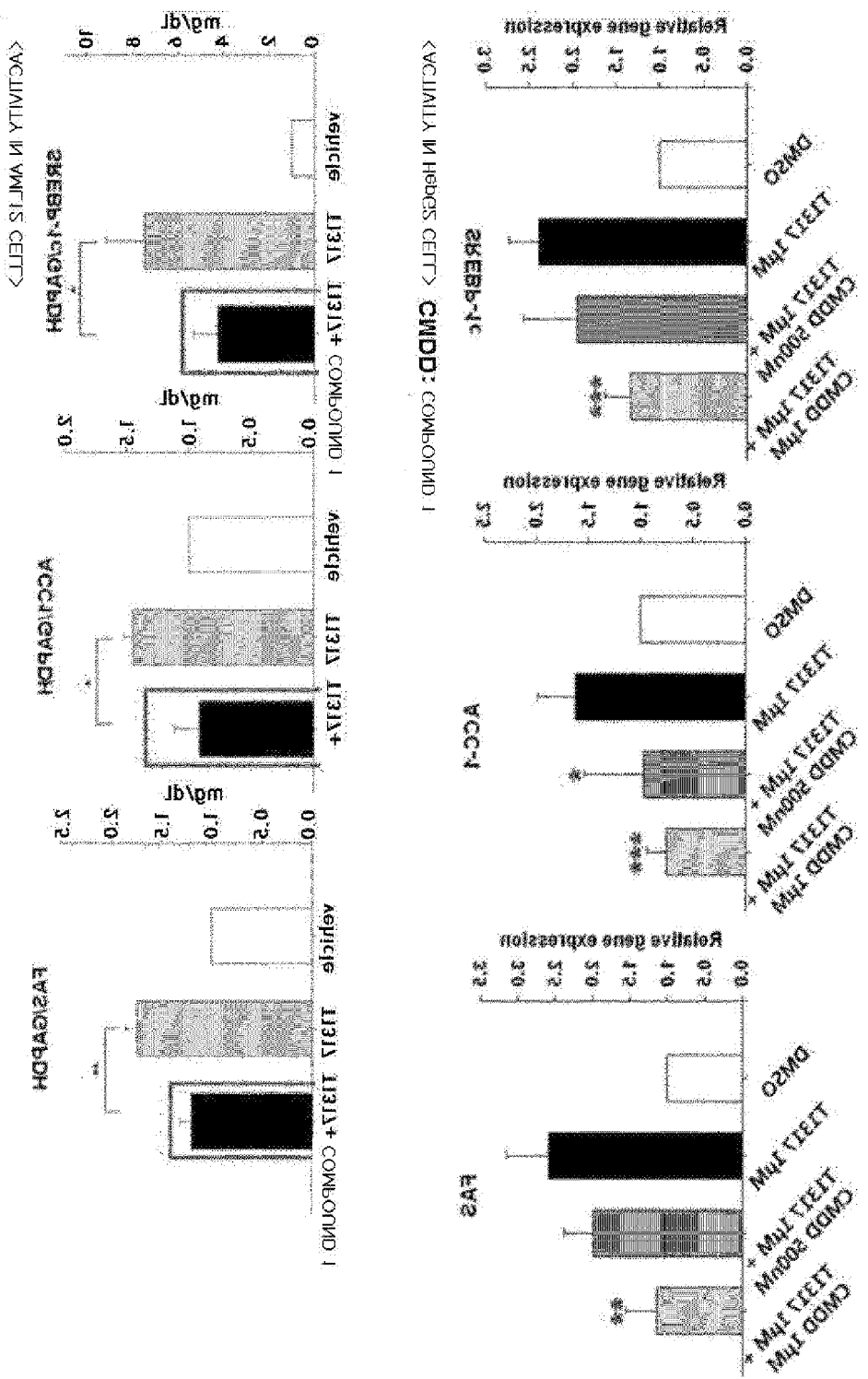
FIG. 14 shows graphs representing gene expression regulation measurement results of the compound 1 of the present invention in liver cells (AML12 and HepG2 cells) in Experimental example 5.

In order to verify efficacy of the developed liver-X-receptor antagonist, the function of regulating gene expression was identified in mouse liver cells and human liver cells. In the present experiment, mouse liver cells, AML 12 cells and human liver cells, and HepG2 cells were used. AML12 cells were cultured in DMEM medium within a cell incubator with 5% carbon dioxide at 37° C. The medium contained 10% fetal bovine serum (FBS), 100 U/ml penicillin, and 100 μg/ml streptomycin. On day 1 of the experiment, AML12 cells are seeded in 6 well plates. On day 2, when the cells were grown to 80% confluency, the medium was replaced by the DMEM medium not containing serum, and then three wells per treatment group were treated with TO901317 and the developed liver-X-receptor antagonist. Wells treated with dimethylsulfoxide having the final concentration of 0.2% were used as a negative control group, and wells treated with TO901317 having the final concentration of 500 nM were used as a positive control group. The compound 1, which was developed to find out the efficacy of the antagonist, was used alone at a concentration of 1 μM, or used together with 500 nM of TO901317. Following the incubation for 18 hours, total liver cell RNAs were extracted using an RNeasy total RNA extraction kit (QIAGEN). The extracted RNAs were quantified, and 1 μg of the extracted RNAs per each sample were used in cDNA synthesis. A Transcriptor First Strand cDNA Synthesis kit (Roche) was used in cDNA synthesis. Genetic analysis was performed on the synthesized liver cell cDNAs using real-time polymerase chain reaction. The cDNAs synthesized for the real-time polymerase chain reaction were mixed with primer selective for ACC1 or Actine gene and QuantiTech Master Mix (QIAGEN). The polymerase chain reaction was performed in 45 cycles of 95° C. for 10 seconds, 60° C. for 15 seconds, and 72° C. for 20 seconds. The polymerase chain reaction was performed in triplicate for each cDNA sample. In order to compare expression amount of each gene per treatment group with one another, Ct values for each sample were obtained using real-time polymerase chain reaction analysis software. The Ct values per each treatment group were compared with the Ct values of the negative control group, and the differences in expression amount of genes were calculated. The difference in expression amount of the interest gene per each treatment group was corrected by the difference in expression amount of GADPH gene. The experimental results showed that the compound 1 inhibited the expression of fatty acid biosynthesis genes causative of the fatty liver, SREBP1c, ACC, and FAS, very effectively (FIG. 14).

Experimental Example 6

Figure 15:
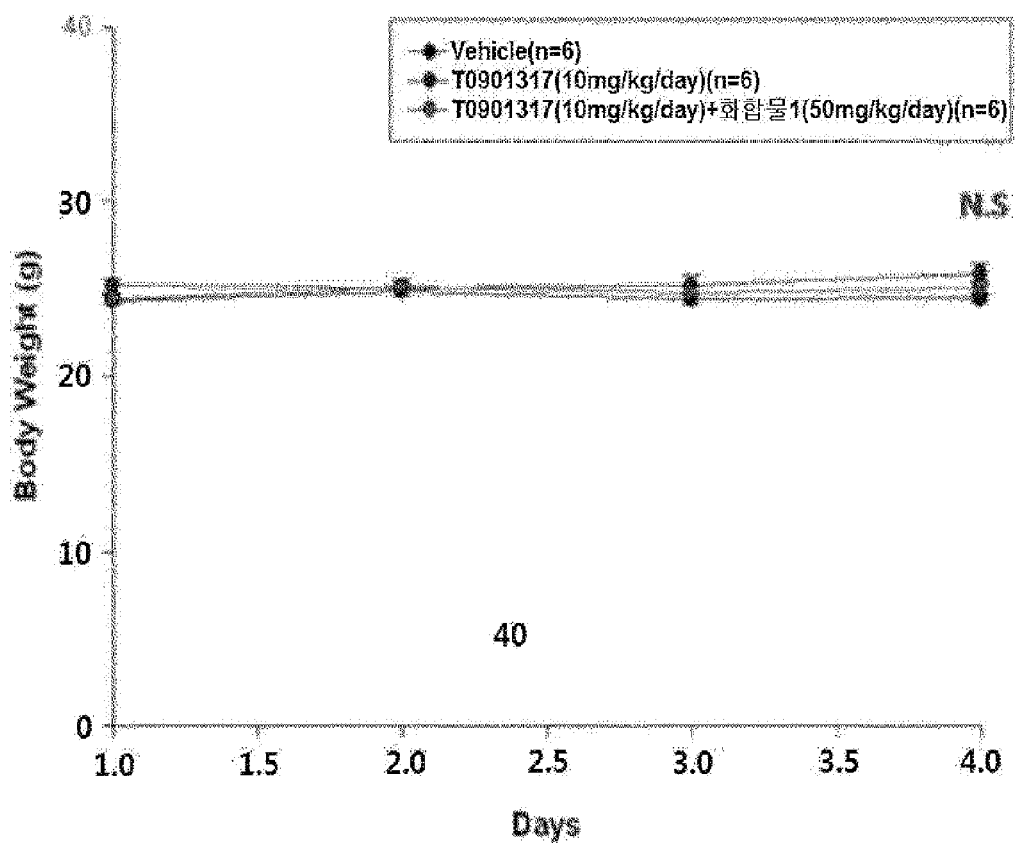
FIG. 15 shows a graph representing body weight changes during periods of administration among treatment and control groups while the compound 1 of the present invention was administered to mice in Experimental example 6.
Figure 16:
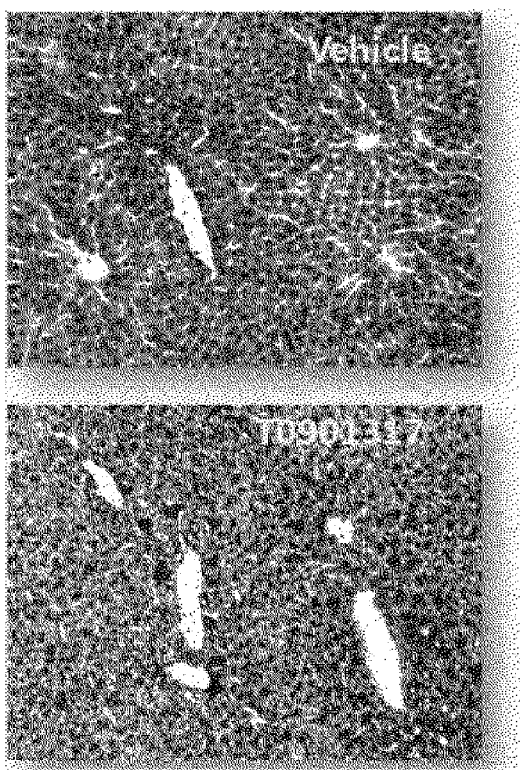
FIG. 16 shows a graph and pictures representing fatty liver inhibitory efficacy results of the compound 1 of the present invention in disease animal model in Experimental example 6.
Figure 16:
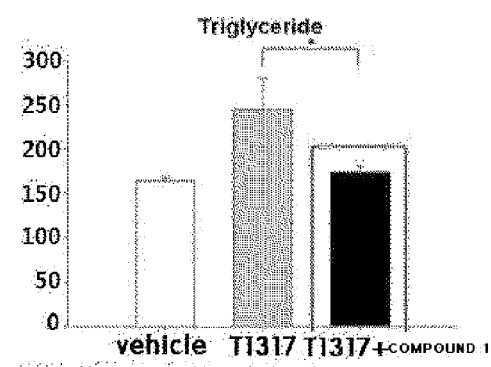
Figure 17:
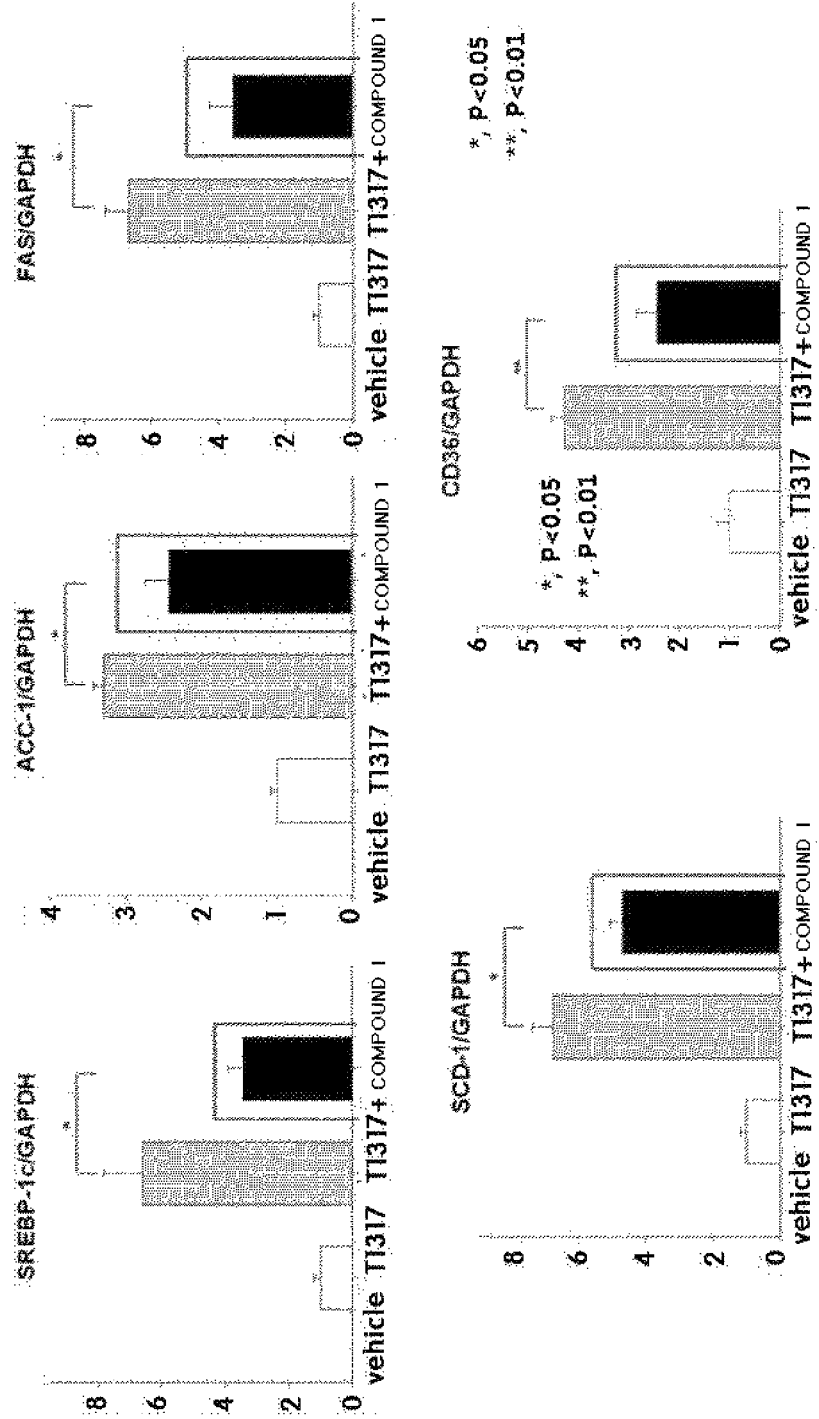
FIG. 17 shows graphs representing gene expression regulation efficacy measurement results exhibited by the compound 1 of the present invention in the disease animal model, after the aforementioned efficacies in these animals were verified through Experimental example 6.

Measurement on Fatty Liver Inhibitory Efficacy of Novel Compounds in Experimental Animal Models In order to verify the fatty liver inhibitory efficacy of the compound 1 developed in the present invention, C57BL/6 mice were used in this experiment. A fatty liver model was constructed by administering T0901317, which generates fatty liver, to 10-week age C57BL/6 mice while feeding the C57BL/6 mice with general feed-additive. The fatty liver inhibitory efficacy of the compound 1 was observed by orally administering this compound. A mouse fed with 0.75% of only carboxymethylcellulose, as a medication deliver, was used for a negative control group, and a mouse fed with only TO901317 was used for a positive control group. In addition, in order to analyze gene expression of C57BL/6 mouse liver, the mouse livers of the negative control group, the positive control group, and the treatment group were extracted and treated with Trizol, to obtain RNAs. The obtained RNAs were quantified using an absorption spectrometer (Nanodrop), and cDNAs were obtained from RNAs having the same amount among respective groups through an RT-PCR method using oligo dT and reverse transcriptase. The real-time polymerase chain reaction was performed using cDNAs, which were obtained for analysis of mRNA change among groups, as templates, and using primers of transporter genes related to fat synthesis and inflow of fat to the liver. The experimental results showed that there was no difference in body weight among the treatment group and the control groups when the compound 1 was administered to fatty liver-induced mice and the compound 1 also exhibited very superior fatty liver inhibitory efficacy in the experimental animal model (FIGS. 15 and 16). In addition, the analytical results on gene expression showed that the compound 1 inhibits the expression of fatty acid synthetic genes, which are causative of fatty liver, and transporter genes of transporting fats to the liver, very effectively (FIG. 17). Accordingly, the compounds of the present invention and derivatives thereof are expected to play a very innovative role in treatment of alcoholic fatty liver, non-alcoholic fatty liver, and fatty liver due to viral infection.

The invention claimed is:
1. A compound of Formula I below, a stereoisomer thereof, an enantiomer thereof, an in vivo-hydrolysable precursor thereof, or a pharmaceutically acceptable salt thereof:

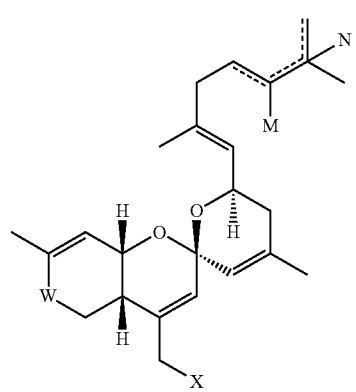

Formula 1 wherein:
W is CO or $CHOR_1$;
X is $N_3$, $NHR_2$, $OR_2$, $SR_2$, $SeR_2$ or $TeR_2$;
$R_1$ and $R_2$ are, independently, selected from hydrogen, straight or branched C1-C8 alkyl, C2-C8 alkenyl, C2-C8 alkynyl, C3-C8 cycloalkyl, C6-$C_{20}$ aryl, C4-$C_{20}$ heteroaryl or $$-\overset{\overset{Y}{\|}}{C}-Z-R_3;$$

Y is O, S or NR₄;
Z is a single bond, NH, O, S, Se or Te;
R₃ and R₄ each are independently selected from hydrogen, straight or branched C1-C8 alkyl, C2-C8 alkenyl, C2-C8 alkynyl, C3-C8 cycloalkyl, C6-C₂₀ aryl, or C4-C₂₀ heteroaryl; and
M and N each are independently hydrogen, OH, or do not exist; wherein a carbon atom bonded to M or N forms a single bond or a double bond with other carbon atoms and the number of double bonds is one or less for each of the carbon atoms.

2. The compound of Formula I, the stereoisomer thereof, the enantiomer thereof, the in vivo-hydrolysable precursor thereof, or the pharmaceutically acceptable salt thereof, of claim 1,
wherein W is CO or CHOR₁;
X is N₃, NHR₂, OR₂, SR₂, SeR₂ or TeR₂;
R₁ and R₂ are, independently, selected from hydrogen, straight or branched C1-C8 alkyl, C2-C8 alkenyl, C2-C8 alkynyl, or $$-\overset{\overset{Y}{\|}}{C}-Z-R_3;$$

Y is O, S or NR₄;
Z is a single bond, NH, O, or S;
R₃ and R₄ each are independently selected from hydrogen, straight or branched C1-C8 alkyl, C2-C8 alkenyl, or C2-C8 alkynyl; and
M and N each are independently hydrogen, OH, or do not exist; wherein a carbon atom bonded to M or N forms a single bond or a double bond with other carbon atoms and the number of double bonds is one or less for each of the carbon atoms.

3. The compound, the stereoisomer thereof, the enantiomer thereof, the in vivo-hydrolysable precursor thereof, or the pharmaceutically acceptable salt thereof, of claim 2,
wherein W is CO or CHOR₁;
X is N₃, OR₂, or SR₂;
R₁ and R₂ each are independently selected from hydrogen, straight or branched C1-C8 alkyl, C2-C8 alkenyl, C2-C8 alkynyl, or $$-\overset{\overset{Y}{\|}}{C}-Z-R_3;$$

Y is O or S;
Z is a single bond;
R₃ is selected from hydrogen, straight or branched C1-C8 alkyl, C2-C8 alkenyl, or C2-C8 alkynyl; and
M and N each are independently hydrogen, OH, or do not exist; wherein a carbon atom bonded to M or N forms a single bond or a double bond with other carbon atoms and the number of double bonds is one or less for each of the carbon atoms.

4. The compound, the stereoisomer thereof, the enantiomer thereof, the in vivo-hydrolysable precursor thereof, or the pharmaceutically acceptable salt thereof, of claim 3, wherein the compound of Formula I is selected from the group consisting of:

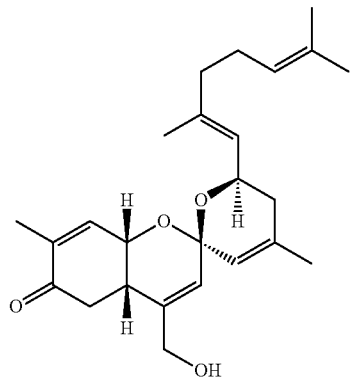

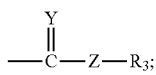
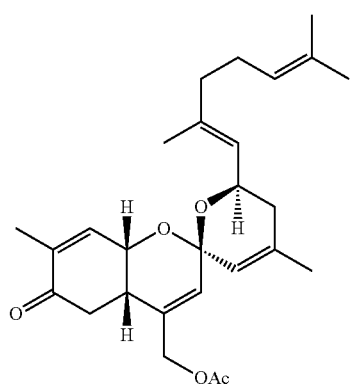

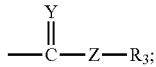
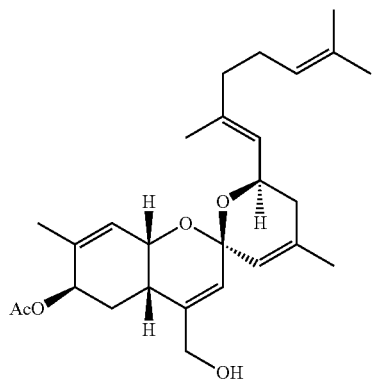

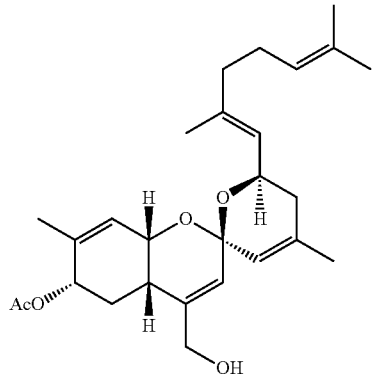

5
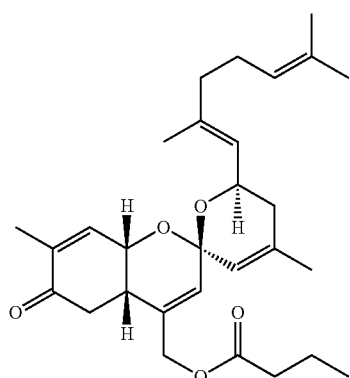

6
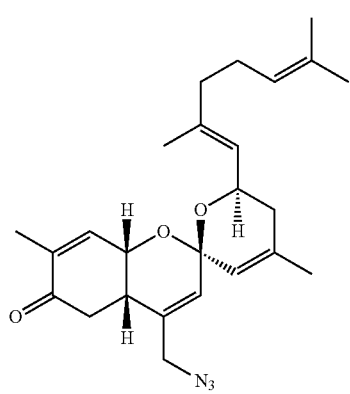

7
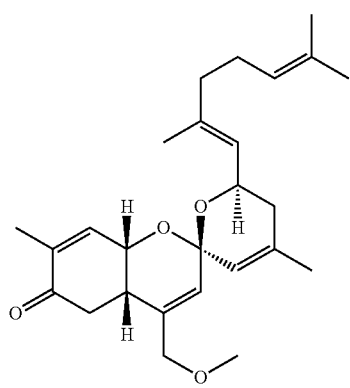

8
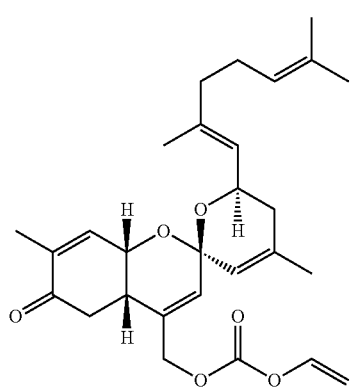

9
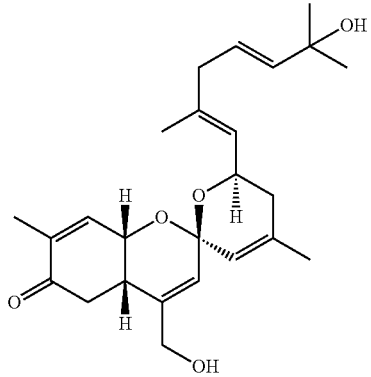

10
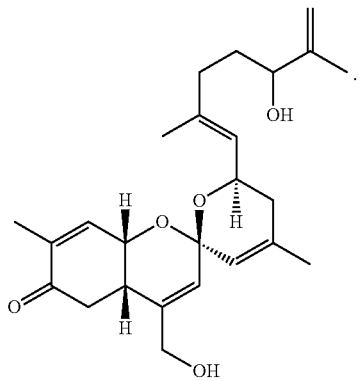

5. A preparation method of the compound of Formula I of claim 1, the method comprising:
(a) cutting and drying the sponge *Phorbas* sp., followed by extraction using C1-C4 alcohol;
(b) partitioning the extract obtained from the step (a) by using water and methylene chloride, and then removing the solvent of the organic layer, followed by again partitioning using n-hexane and a mixture solution of methanol and water; and
(c) removing the solvent of the methanol aliquot layer obtained from the step (b), and then obtaining an aliquot by chromatography using silica as a stationary phase and using a methanol solution as an eluent, the methanol solution containing or not containing 20 weight % or less of water based on total weight of the methanol solution.

6. The method of claim 5, wherein in the step (a), freeze-drying is used for the drying, and methanol is used for the C1-C4 alcohol.

7. The method of claim 5, wherein in the step (b), the mixture solution of methanol and water contains 60-90 weight % of methanol and 10-40 weight % of water based on total weight of the solution.

8. The method of claim 5, wherein in the step (c), the chromatography is performed once or more in the order of from the eluent having the highest polarity to the eluent having the lowest polarity, by using a mixture solution of water and methanol having a higher polarity as the eluent, before using the methanol solution containing or not containing 20 weight % or less of water based on total weight of the eluent as the eluent.

9. The method of claim 5, further comprising (d) purifying the aliquot obtained from the step (c), wherein the purifying is performed by a high performance liquid chromatography (HPLC), and as the eluent, a mixture liquid of 50-80 weight % of acetonitrile (ACN) and 20-50 weight % of water based on total weight of the eluent is used.

10. A pharmaceutical composition comprising as an active ingredient the compound of Formula I of claim 1, the stereoisomer thereof, the enantiomer thereof, the in vivo-hydrolysable precursor thereof, or the pharmaceutically acceptable salt thereof, and a pharmaceutically acceptable carrier.

11. The pharmaceutical composition according to claim 10 for treating a condition selected from osteoporosis, fatty liver, and obesity.

12. The pharmaceutical composition of claim 10 for antagonizing liver-X-receptor (LXR) activity.

* * * * *